United States Patent
Cunningham, Jr.

(10) Patent No.: US 8,373,023 B2
(45) Date of Patent: Feb. 12, 2013

(54) BIOCHEMICAL ROUTE TO ASTAXANTHIN

(75) Inventor: Francis X. Cunningham, Jr., Chevy Chase, MD (US)

(73) Assignee: University of Maryland, College Park, MD (US)

( * ) Notice: Subject to any disclaimer, the term of this patent is extended or adjusted under 35 U.S.C. 154(b) by 823 days.

(21) Appl. No.: 12/226,426

(22) PCT Filed: Apr. 20, 2007

(86) PCT No.: PCT/US2007/009803
§ 371 (c)(1),
(2), (4) Date: Mar. 24, 2009

(87) PCT Pub. No.: WO2007/124135
PCT Pub. Date: Nov. 1, 2007

(65) Prior Publication Data
US 2010/0008871 A1    Jan. 14, 2010

Related U.S. Application Data

(60) Provisional application No. 60/793,645, filed on Apr. 21, 2006.

(51) Int. Cl.
| | |
|---|---|
| C12N 1/13 | (2006.01) |
| C12N 5/10 | (2006.01) |
| C12N 5/14 | (2006.01) |
| C12N 15/15 | (2006.01) |
| C12N 15/16 | (2006.01) |
| C12N 15/21 | (2006.01) |
| C12N 15/27 | (2006.01) |
| C12N 15/52 | (2006.01) |
| C12N 15/82 | (2006.01) |

(52) U.S. Cl. ........ 800/282; 800/296; 800/298; 435/41; 435/183; 435/252.3; 435/320.1; 435/325; 435/419; 435/468; 435/471; 536/23.1; 536/23.6

(58) Field of Classification Search ....... 800/278–320.1; 536/23.2–23.6
See application file for complete search history.

(56) References Cited

PUBLICATIONS

Breitenbach, J. et al., *FEMS Microbiology Letters*, 140:241-246 (1996).
Breitenbach, J. et al., *Z. Naturforsch*, 56c:915-917 (2001).
Chayen, N. et al., *Acta Cryst.*, D59:2072-2082 (2003).
Choi, S. et al., *Marine Biotechnology*, 7:515-522 (2005).
Cunningham, F. et al., *The Plant Cell*, 8:1613-1626 (1996).
Czeczuga, B., *Biochemical Systematics and Ecology*, 15(3):303-306 (1987).
Egger, K, *Phytochemistry*, 4:609-618 (1965).
Fernández-González, B. et al., *The Journal of Biological Chemistry*, 272(15):9728-9733 (1997).
Fraser, P. et al., *Eur. J. Biochem.*, 252:229-236 (1998).
Grung, M. et al., *Biochemical Systematics and Ecology*, 21(8):757-763 (1993).
Hannibal, L. et al., *Journal of Bacteriology*, 182(13):3850-3853 (2000).
Johnson, E., *Critical Reviews in Biotechnology*, 11(4):297-326 (1991).
Johnson, E., *Int Microbiol*, 6:169-174 (2003).
Kajiwara, S. et al., *Plant Molecular Biology*, 29:343-353 (1995).
Kamata, T. et al., *Nippon Suisan Gakkaishi*, 56(5):789-794 (1990).
Lorenz, R. et al., *Tibtech*, 18:160-167 (2000).
Lotan, T. et al., *FEBS Letters*, 364:125-128 (1995).
Mann, V. et al., *Nature Biotechnology*, 18:888-892 (2000).
Masamoto, K. et al., *Plant Cell Physiol.*, 42(12):1398-1402 (2001).
Mercadante, A. et al., Carotenoids Handbook, Birkhäuser Verlag, 3 pages, (2004).
Misawa, N. et al., *Biochemical and Biophysical Research Communications*, 209(3):867-876 (1995).
Misawa, N. et al., *Journal of Bacteriology*, 177(22):6575-6584 (1995).
Orosa, M. et al., *Journal of Applied Phycology*, 12:553-556 (2000).
Ralley, L. et al., *The Plant Journal*, 39:477-486 (2004).
Ravanello, M. et al., *Metabolic Engineering*, 5:255-263 (2003).
Renstrøm, B. et al., *Biochemical Systematics and Ecology*, 9(4):249-250 (1981).
Seybold, A. et al., *Nature*, 184(4700):1714-1715 (1959).
Shahidi, F. et al., *Critical Review in Food Science*, 38(1):1-67 (1998).
Shewmaker, C. et al., *The Plant Journal*, 20(4): 401-412 (1999).
Stålberg, K. et al., *The Plant Journal*, 36:771-779 (2003).
Steiger, S. et al., *Biotechnology Letters*, 26:813-817 (2004).
Tanaka, Y. et al., *Comp. Biochem. Physiol.*, 54B:391-393 (1976).
Visser, H. et al., *FEMS Yeast Research*, 4:221-231 (2003).
Cunningham, Jr. et al., "Elucidation of the Pathway to Astaxanthin in the Flowers of *Adonis aestivalis*," *The Paint Cell*, 23, 3055-3069 (2011).
Dym et al., "Sequence-structure analysis of FAD-containing proteins," *Protein Science*, 10, 1712-1728 (2001).
Emanuelsson et al., "Locating proteins in the cell using TargetP, SignalP and related tools," *Nature Protocols*, 2 (4), 953-971 (2007).
Heyn et al., "The annual species of *Adonis* (ranunculaceae)—a polyploid complex," *Plant Systematics and Evolution 168*, 181-193 (1989).
Wierenga et al., "Prediction of the Occurrence of the ADP-binding (βαβ-fold in Proteins, Using an Amino Acid Sequence Fingerprint," *J. Mol. Biol.*, 187, 101-107 (1986).

*Primary Examiner* — Russell Kallis
(74) *Attorney, Agent, or Firm* — Leydig, Voit & Mayer, Ltd.

(57) ABSTRACT

Two sequences of a nucleic acid isolated from a cDNA library of the flowering plant *Adonis aestivalis* is disclosed (SEQ ID NO: 5). The first DNA sequence, referred to as AdKC28, encodes for a polypeptide (SEQ ID NO: 6) that acts in conjunction with polypeptides encoded by either one of two other closely-related *Adonis aestivalis* cDNAs, AdKeto1 (SEQ ID NO: 1) and AdKeto2 (SEQ ID NO: 2), to convert β-carotene (β,β-carotene) into astaxanthin (3,3'-dihydroxy-4,4'-diketo-β, β-carotene). A second DNA sequence, referred to as AdKCl 7 is also disclosed (FIG. 9). Together, these *Adonis aestivalis* cDNAs, when operably linked to promoters appropriate to the transgenic host, enable the production of astaxanthin and other carotenoids with 3-hydroxy-4-keto-β-rings in a variety of host cells and organisms.

34 Claims, 10 Drawing Sheets

```
AGCAATCTCAGTGTTCAGTACAAGTTATTCTTTCCACAAGAATCTCTTGTTGCACTCAAA      60
ACAAGACATTCTCAACCGCCCATGTTTGCTCTTCTCTCCAGTTGTGGTGGAGTCGCCTAT     120
GAGAAAGAAAAAGACACATCGTGCTGCATGTATCTGCTCTGTTGCAGAGAGAACAAGGAA     180
CCTTGATATTCCTCAAATTGAAGAAGAGGAAGAGAACGAGGAAGAACTAATAGAACAGAC     240
GGATTCTGGCATAATTCATATAAAGAAAACGCTAGGGGGGAAACAATCAAGACGGTCCAC     300
TGGCTCCATTGTCGCACCCGTATCTTGTCTTGGGATCCTTTCAATGATCGGACCTGCTGT     360
TTACTTCAAGTTTTCACGGCTAATGGAGTGTGGAGATATTCCTGTCGCAGAAATGGGGAT     420
TACGTTTGCCGCCTTTGTTGCTGCTGCGATTGGCACGGAATTTTTGTCAGGATGGGTTCA     480
CAAAGAACTCTGGCACGATTCTTTGTGGTACATTCACAAGTCTCACCATAGGTCACGAAA     540
AGGCCGCTTCGAGTTCAATGATGTGTTTGCTATTATTAACGCGCTTCCTGCTATTGCTCT     600
TATCAATTATGGATTCTCAAATGAAGGCCTCCTTCCTGGAGCCTGCTTTGGTACCGGTCT     660
TGGAACGACAGTCTGTGGCATGGCTTACATTTTTCTTCACAATGGCCTTTCACACCGAAG     720
GTTCCCAGTAGGGCTTATTGCAAACGTCCCTTATTTCCACAAGCTGGCTGCAGCTCACCA     780
AATCCATCACTCAGGAAAATTTCAGGGTGTACCATTTGGCCTGTTCCTTGGACCCCAGGA     840
ATTGGAAGAAGTAAGAGGAGGCACTGAAGAATTGGAGAGGGTGATCAGTCGTACAGCTAA     900
ACGAACGCAATCATCTACATGAATCAACTCTTTTACATTTATGAGGTTTTAGTTTATCGG     960
TGTTACAAGTCACACATTTGTGTCGTTGTAGTAATTCAAAGTTACCATACTCTTTTTTAG    1020
AATTTTTTTTGATGTATAGGTCGCGGAGTTACGGTTACAAAGGCCAAATCTATTGTTGT    1080
GGAATTCCATTATTAAAAATAAAAATTAGAGTTTGTAGTTTTATCTGGTGATCAATATCA    1140
ATATATATTAATTAAAGCAAAAAAAAAAAAAAAAAA    1176
```

FIG. 2.

```
ATGGCAGCAGCAATTTCAGTGTTCAGTTCAGGTTATTCTTTCTACAAGAATCTCTTGTTG     60
GACTCAAAACCAAATATTCTCAAACCCCCATGCCTGCTATTCTCTCCAGTTGTGATCATG    120
TCGCCTATGAGAAAGAAAAGAAACATGGTGATCCATGTATCTGCTCCGTTGCAGGGAGA    180
ACAAGGAACCTTGATATTCCTCAAATTGAAGAAGAGGAAGAGAATGTGGAAGAACTAATA    240
GAACAGACCGATTCTGACATAGTGCATATAAAGAAAACACTAGGGGGGAAACAATCAAAA    300
CGGCCCACTGGCTCCATTGTCGCACCCGTATCTTGTCTTGGGATCCTTTCAATGATTGGA    360
CCTGCTGTTTACTTCAAGTTTTCACGGCTAATGGAGGGTGGAGATATACCTGTAGCAGAA    420
ATGGGGATTACGTTTGCCACCTTTGTTGCTGCTGCTGTTGGCACGGAGTTTTTGTCAGCA    480
TGGGTTCACAAAGAACTCTGGCACGAGTCTTTGTGGTACATTCACAAGTCTCACCATCGG    540
TCACGAAAAGGCCGCTTCGAGTTCAATGATGTGTTTGCTATTATTAACGCGCTTCCCGCT    600
ATTGCTCTTATCAATTATGGATTCTCCAATGAAGGCCTCCTTCCTGGAGCGTGCTTTGGT    660
GTCGGTCTTGGAACAACAGTCTGTGGTATGGCTTACATTTTTCTTCACAATGGCCTATCA    720
CACCGAAGGTTCCCAGTATGGCTTATTGCGAACGTCCCTTATTTCCACAAGCTGGCTGCA    780
GCTCACCAAATACACCACTCAGGAAAATTTCAGGGTGTACCATTTGGCCTGTTCCTTGGA    840
CCCAAGGAATTGGAAGAAGTAAGAGGAGGCACTGAAGAGTTGGAGAGGGTAATCAGTCGT    900
ACAACTAAACGAACGCAACCATCTACCTGAATCAATTTTTTACATATATAAGGTTTAG    960
TTTATCGGTGTTATAAAATCACACATCCGTATCGTTTTAGTAAGTCAAAGTTAAGATACT    1020
TCCTTCTTAGAATATTTTTGATGTATAGGTCGCGGATATACTGTTACACTATTCGTTGT    1080
GGAATTCCATTATAAAAAAATAAAAAAAAAAAAAAAAA    1120
```

FIG. 3.

```
                    *         20         *         40         *         60
AdKeto1 : ---ATSVESTSYSEEKNIELHSKODEENRPCLEESPVVVESPLRKKKTERAACICSVAER :  57
AdKeto2 : MAAATSVESSGYSEYKNIELIDSKPNELKPPCLEESPVVIMSPLRKKNKEGDPCICSVAGR :  60

*         80         *        100         *        120
AdKeto1 : IRNIDIPDIEEEIMENEEEIEQIDSGIIELKKVELGCKQSRRSTGSIVAPVSCLCIESMIC : 117
AdKeto2 : IRNIDIPDIEEEIMQVEELIEQIDSDIVELKKVLGCKQSKRPTGSIVAPVSCLCIESMIC : 120

*        140         *        160         *        180
AdKeto1 : PAVYIKESRIMECGDIPVAEMGILIEAAEVAAATGIEEISGUVEKELVEDSLWYIHKSEHR : 177
AdKeto2 : PAVYIKESRIMECGDIPVAEMGILIEATEVAAAVGIEEILSAEVEKELVEISLWYIHKSEHR : 180

*        200         *        220         *        240
AdKeto1 : SRKGRIEENDVEAIINAIPATAIINYGESNEGIIPCACECTELGIIVCGMAYIEIHNGIS : 237
AdKeto2 : SRKGRIEENDVEAIINAIPATAIINYGESNEGIIPCACECVGLGIIVCGMAYIEIHNGIS : 240

*        260         *        280         *        300
AdKeto1 : ERRIPVGITANVPYFHKLAAAHOIHHSCKEOGVPECIEICEOLEEVRGGIEELERVISR : 297
AdKeto2 : ERRIPVWITANVPYFHKLAAAHOIHHSCKEOGVPECIEICEKELEEVRGGIEELERVISR : 300

AdKeto1 : TAKRIOSSI : 306
AdKeto2 : TTKRIOPSI : 309
```

FIG. 4

```
GAAGAACATTACATGGCTCCTGTTCTCCTTGGATTGAAACCAACTCTCTCCACTGGAAGC    60
GTCGTCAAAGAGACTAATGTAGGAAGCACACTTGCTAGTCCCCTTAACAAAACCCAGAAT   120
TCAAGGGTTTTGGTTTTGGGCGGAACAGGGAAGGTCGGTGGTTCCACAGCTTTGGCTCTC   180
TCCAAGTTCTCACCTGACCTCAGGCTTGTGATTGGAGGTCGAAACAGGGAGAAAGGTGAT   240
GCTGTAGTGTCTAAACTAGGAGAAAACTCCGAGTTTGTTGAAGTCAACGTTGACAGTGTG   300
AGATCTTTAGAATCTGCTCTCGAAGATGTGGACCTTGTAGTTCATGCAGCTGGACCTTTT   360
CAACAAGCGGAGAAGTGCACTGTTCTAGAAGCTGCAATATCTACCAGGACGGCCTATGTG   420
GATGTATGTGATAATACAAGTTATTCCATGCAAGCAAAGTCTTTTCATGATAAAGCAGTG   480
GCTGCCAACGTTCCTGCCATAACAACTGCTGGAATTTTCCCTGGAGTGAGCAATGTGATA   540
GCAGCTGAGCTAGTGCGATCAGCAAGAGATGAAAACACTGAACCTCAAAGACTAAGATTC   600
TCCTATTTTACCGCGGGTTCTGGTGGTGCTGGTCCAACGTCGTTAGTTACTAGCTTCTTG   660
CTTCTTGGTGAAGAGGTTGTTGCTTACAGTGAAGGCGAAAAGTCGAATTAAAGCCTTAT   720
ACAGGGAAGCTTAACATTGACTTCGGGAAGGGAGTTGGGAAAAGAGACGTTTATTTGTGG   780
AACTTGCCGGAAGTAAGAAGTGGTCATGAGATCTTAGGAGTACCAACTGTGAGTGCTCGA   840
TTCGGTACTGCACCTTTCTTCTGGAATTGGGCGATGGTAGCTATGACAACTCTCCTTCCT   900
CCTGGTATTCTGAGAGACAGAAATAAAATCGGAATGTTGGCAAATTTTGTGTACCCTTCT   960
GTACAAATTTTTGATGGGATTGCAGGAGAATGTCTTGCAATGCGGGTTGATTTAGAGTGC  1020
GCAAATGGGCGCAATACTTTTGGTATACTCAGTCATGAACGTCTCTCTGTATTAGTGGGA  1080
ACTTCAACTGCGGTGTTTGCTATGGCAATTCTTGAAGGAAGTACGCAGCCTGGAGTTTGG  1140
TTTCCAGAAGAGCCTGGAGGGATTGCAATAAGTGACAGAGAGTTACTTCTACAACGAGCA  1200
TCACAAGGAGCGATTAACTTCATTATGAAGCAGTAGAGTAATAGATTGGATTATTCATTA  1260
TGTAGCCCAGAATGACATTATTTACATGTAATGTTGCTTCTATGTATCAATAACATAAAT  1320
CACAAGTCATTCGTATTTATATAAGTATTCAGTCCATATCTGGGAGCAAAAAAAAAAAA  1380
AAAAAAA   1387
```

FIG. 5.

```
MAPVLLGLKPTLSTGSVVKETNVGSTLASFLNKTQNSRVLVLGGTGKVGGSTALALSKFS    60
PDLRLVIGGRNREKGDAVVSKLGENSEFVEVNVDSVRSLESALEDVDLVVHAAGPFQQAE   120
KCTVLEAAISTRTAYVDVCDNTSYSMQAKSFHDKAVAANVPAITTAGIFPGVSNVIAAEL   180
VRSARDENTEPQRLRFSYFTAGSGGAGPTSLVTSFLLLGEEVVAYSEGEKVELKPYTGKL   240
NIDFGKGVGKRDVYLWNLPEVRSGHEILGVPTVSARFGTAPFFWNWAMVAMTTLLPPGIL   300
RDRNKIGMLANFVYPSVQIFDGIAGECLAMRVDLECANGRNTFGILSHERLSVLVGTSTA   360
VFAMAILEGSTQPGVWFPEEPGGIAISDRELLLQRASQGAINFIMKQ   407
```

FIG. 6.

```
                  *         20         *         40         *         60
AdKC28     : --MAPVILGLKPILSTGSVVKETNVGSTLASPLNKTONSRVLVLGGTCKVGGSTALVSK   :  58
At1g50450  : MTRALLLOPYRAIVRAASSRETQYDGVPEVKFSDPSRNYRVLVLGGTCRVGGSTATVSK   :  60

*         80         *        100         *        120
AdKC28     : FSPDLRLVIGERNREKGDAVVSRIGINSELVEVNVDSVRSESSAIEDVDLVVHAAGPHQQ   : 118
At1g50450  : LCPELKIVVGGRNRDKGEAMYARLIGNSLTSOVDINDARMLETSIRDVDLVVHAAGPHQQ   : 120

*        140         *        160         *        180
AdKC28     : AEKGIVLKEAAISIRIAYVDVGDNTSVSMQAKSFHDKLVAANVPAILILAGIEPGVSNVIAA   : 178
At1g50450  : SPRGIVLKFAAIKKIAYLDVGDDUSPAFRAKSLEAEIIDPNIPAILILAGIYPGVSNVMAA   : 180

*        200         *        220         *        240
AdKC28     : BLVRSARDDN-TSPORIETSYYIAGSGGACPTSIVISLILEDRVVAVSEGEKVEIRPYT   : 237
At1g50450  : EMVAAARSEDKGKPEKIRESYYTAGTGGACPTLIATSLTLEDAVTAYKOETKVKIRPYS   : 240

*        260         *        280         *        300
AdKC28     : EKLNIDFGKGVGKRDVYIWNIPEVRSGHBILGVPTIVSARFGTAPHTNTAMVAIITITIIP   : 297
At1g50450  : GMITVDEGKGIRKRDVYILNLPEVRSTHDVLGVPTIVPARFGTAPHTNTGMEILILILES   : 300

*        320         *        340         *        360
AdKC28     : GIIRDRNKIGMLANPVYPSVQIEDGIAGECLAMRVDIECANGRNTEGILSHERESVLVGT   : 357
At1g50450  : EVIRDRTIVQQMVELFDEMVRAMDGIACERVSMRVDLEGSDGRTIVELFSHKKESVSVGV   : 360

*        380         *        400         *        420
AdKC28     : SHTAVGAMAILEGSTDPGVWEPEILGIAISDREIEIGIASDGAINIIIMKQ----------  : 407
At1g50450  : SHTAARVAAMIEGSTDPGVWEPEIPQGIAVEARDVILIKRASDGTFNEILNKPPWMVETEPK  : 420

AdKC28     : --------                :  -
At1g50450  : EVVLGIYV                : 428
```

FIG. 7.

>Adonis aestivalis cDNA AdKC17
```
GAACATTACATGGCGCGTGTCTTCCTTGGATTGAAACCAACTCTCTCCACTGGAAGCTCG    60
TCAAAGAGACTACTGTAGGAAACACACTTGTTAGTCCCCTTAACAAAACCCAGAATTCAA   120
GGGTTTTGGTTTTGGGCGGAACAGGGAAGGTCGGTGGTTCCACAGCTTTCGCTCTCTCCA   180
AGTTCTCACCTGACCTCAGGCTTGTGATTGGAGGTCGAAACAGGGAGAAAGGTGATGCTG   240
TAGTGTCTAAACTAGGAGAAAACTCCGAGTTTGTTGAAGTCAACGTTGACAGCATGAGAT   300
CTTTAGAATCTGCCTTCAAAGATGTGGATCTTGTAGTTCATGCAGCTGGACCTTTTCAAC   360
AAGCGGAGAAGTGCACTGTTCTAGAAGCTGCAATATCTACCAGGACGGCCTATGTGGATG   420
TATGTGATAATACAAGTTACTCCATGCAAGCTAAGTCTTTTCATGATAAAGCAGTGGCTG   480
CCAACGTTCCTGCCATAACAACTGCTGGAATTTTCCCTGGAGTGAGCAATGTGATAGCAG   540
CTGAGCTAGTGCGATCAGCAAGAGATGAAAACACTGAACCTCAAAGACTAAGATTCTCCT   600
ATTTTACCGCGGGTTCTGGTGGTGCTGGTCCAACCTCGTTAGTTACTAGCTTTTTGCTTC   660
TTGGTGAAGAGGTTGTTGCTTACAGTGAAGGTGAAAAGGTCGAATTAAAGCCTTATACAG   720
GGAAGCTTAACATTGACTTCGGGAAGGGAGTTGGAAAAAGAGACGTTTATTTGTGGAACT   780
TACCCGAAGTAAGAAGTGGTCATGAGATCTTAGGAGTACCAACTGTGAGTGCTCGATTCG   840
GTACTGCACCTTTCTTCTGGAATTGGGCGATGGTAGCTATGACAAGTCTCCTTCCTCCTG   900
GTATTCTGAGAGACAGAAATATAATTGAAAAGTTGGCAAATTTTGTCTACCCTTCTGTAC   960
AAGTTTTTGATGGTATTGCAGGAGAATGTCTGGCTATGCGGGTTGATTTGGAGTGCGCAA  1020
ATGGGCGCAACACTTCTGCTATACTCAGTCACGAACGTCTCTCTGAATTAGTGGGAACTT  1080
CAACCGCGGTGTTTGCTTTGGCAATTCTTGAGGGAAGTACACAGGCTGGTGTTTGGTTTC  1140
CAGAAGAGCCCGAGGGGATTGCAGTAGGAGACAGAGAATTACTTCTAAAACGAGCATCAC  1200
AAGGAGCTATTAACTTCATTATGAAGCAGTAGAGCAATAGATTGGATTATTCATTATGTA  1260
GCCAAGAATAACATTATTTACATGTAATGTTCCTTCTATGTATCAATAACATACATTTTA  1320
CATGTTATCTCTAATGGAAATTTTAGATGAACTCAAAAAAAAAAAAAAAAAAA        1375
```

FIG. 9

>Translation of AdKC17; bases 3-1229
```
TLHGACLPWIETNSLHWKLVKETTVGNTLVSPLNKTQNSRVLVLGGTGKVGGSTAFALSK    60
FSPDLRLVIGGRNREKGDAVVSKLGENSEFVEVNVDSMRSLESAFKDVDLVVHAAGPFQQ   120
AEKCTVLEAAISTRTAYVDVCDNTSYSMQAKSFHDKAVAANVPAITTAGIFPGVSNVIAA   180
ELVRSARDENTEPQRLRFSYFTAGSGGAGPTSLVTSFLLLGEEVVAYSEGEKVELKPYTG   240
KLNIDFGKGVGKRDVYLWNLPEVRSGHEILGVPTVSARFGTAPFFWNWAMVAMTSLLPPG   300
ILRDRNIIEKLANFVYPSVQVFDGIAGECLAMRVDLECANGRNTSAILSHERLSELVGTS   360
TAVFALAILEGSTQAGVWFPEEPEGIAVGDRELLLKRASQGAINFIMKQ            409
```

FIG. 10

Comparison of nucleotide sequences of *AdKC28* and *AdKC17*    FIG. 11A

*AdKC28* (Query) vs. *AdKC17* (Sbjct)
Identities = 1255/1314 (95%), Gaps = 1/1314 (0%)

```
Query    4    GAACATTACATGGCTCCTGTTCTCCTTGGATTGAAACCAACTCTCTCCACTGGAAGCGTC    63
              |||||||||||||| | |||  |||||||||||||||||||||||||||||||||||| ||
Sbjct    1    GAACATTACATGGCGCGTGTCTTCCTTGGATTGAAACCAACTCTCTCCACTGGAAGC-TC    59

Query   64    GTCAAAGAGACTAATGTAGGAAGCACACTTGCTAGTCCCCTTAACAAAACCCAGAATTCA   123
              ||||||||||||| |||||||||  ||||||| |||||||||||||||||||||||||||
Sbjct   60    GTCAAAGAGACTACTGTAGGAAACACACTTGTTAGTCCCCTTAACAAAACCCAGAATTCA   119

Query  124    AGGGTTTTGGTTTTGGGCGGAACAGGGAAGGTCGGTGGTTCCACAGCTTTGGCTCTCTCC   183
              |||||||||||||||||||||||||||||||||||||||||||||||||||| |||||||
Sbjct  120    AGGGTTTTGGTTTTGGGCGGAACAGGGAAGGTCGGTGGTTCCACAGCTTTCGCTCTCTCC   179

Query  184    AAGTTCTCACCTGACCTCAGGCTTGTGATTGGAGGTCGAAACAGGGAGAAAGGTGATGCT   243
              ||||||||||||||||||||||||||||||||||||||||||||||||||||||||||||
Sbjct  180    AAGTTCTCACCTGACCTCAGGCTTGTGATTGGAGGTCGAAACAGGGAGAAAGGTGATGCT   239

Query  244    GTAGTGTCTAAACTAGGAGAAAACTCCGAGTTTGTTGAAGTCAACGTTGACAGTGTGAGA   303
              |||||||||||||||||||||||||||||||||||||||||||||||||||||  |||||
Sbjct  240    GTAGTGTCTAAACTAGGAGAAAACTCCGAGTTTGTTGAAGTCAACGTTGACAGCATGAGA   299

Query  304    TCTTTAGAATCTGCTCTCGAAGATGTGGACCTTGTAGTTCATGCAGCTGGACCTTTTCAA   363
              ||||||||||||||  || |||||||||||| ||||||||||||||||||||||||||||
Sbjct  300    TCTTTAGAATCTGCCTTCAAAGATGTGGATCTTGTAGTTCATGCAGCTGGACCTTTTCAA   359

Query  364    CAAGCGGAGAAGTGCACTGTTCTAGAAGCTGCAATATCTACCAGGACGGCCTATGTGGAT   423
              ||||||||||||||||||||||||||||||||||||||||||||||||||||||||||||
Sbjct  360    CAAGCGGAGAAGTGCACTGTTCTAGAAGCTGCAATATCTACCAGGACGGCCTATGTGGAT   419

Query  424    GTATGTGATAATACAAGTTATTCCATGCAAGCAAAGTCTTTTCATGATAAAGCAGTGGCT   483
              |||||||||||||||||||| ||||||||||||| |||||||||||||||||||||||||
Sbjct  420    GTATGTGATAATACAAGTTACTCCATGCAAGCTAAGTCTTTTCATGATAAAGCAGTGGCT   479

Query  484    GCCAACGTTCCTGCCATAACAACTGCTGGAATTTTCCCTGGAGTGAGCAATGTGATAGCA   543
              ||||||||||||||||||||||||||||||||||||||||||||||||||||||||||||
Sbjct  480    GCCAACGTTCCTGCCATAACAACTGCTGGAATTTTCCCTGGAGTGAGCAATGTGATAGCA   539

Query  544    GCTGAGCTAGTGCGATCAGCAAGAGATGAAAACACTGAACCTCAAAGACTAAGATTCTCC   603
              ||||||||||||||||||||||||||||||||||||||||||||||||||||||||||||
Sbjct  540    GCTGAGCTAGTGCGATCAGCAAGAGATGAAAACACTGAACCTCAAAGACTAAGATTCTCC   599

Query  604    TATTTTACCGCGGGTTCTGGTGGTGCTGGTCCAACGTCGTTAGTTACTAGCTTCTTGCTT   663
              ||||||||||||||||||||||||||||||||||||  ||||||||||||| |||| |||
Sbjct  600    TATTTTACCGCGGGTTCTGGTGGTGCTGGTCCAACCTCGTTAGTTACTAGCTTTTTGCTT   659

Query  664    CTTGGTGAAGAGGTTGTTGCTTACAGTGAAGGCGAAAAAGTCGAATTAAAGCCTTATACA   723
              |||||||||||||||||||||||||||||||| |||||| ||||||||||||||||||||
Sbjct  660    CTTGGTGAAGAGGTTGTTGCTTACAGTGAAGGTGAAAAGGTCGAATTAAAGCCTTATACA   719

Query  724    GGGAAGCTTAACATTGACTTCGGGAAGGGAGTTGGGAAAAGAGACGTTTATTTGTGGAAC   783
              |||||||||||||||||||||||||||||||| |||||||||||||||||||||||||||
Sbjct  720    GGGAAGCTTAACATTGACTTCGGGAAGGGAGTTGGAAAAAGAGACGTTTATTTGTGGAAC   779

Query  784    TTGCCGGAAGTAAGAAGTGGTCATGAGATCTTAGGAGTACCAACTGTGAGTGCTCGATTC   843
              || || ||||||||||||||||||||||||||||||||||||||||||||||||||||||
Sbjct  780    TTACCCGAAGTAAGAAGTGGTCATGAGATCTTAGGAGTACCAACTGTGAGTGCTCGATTC   839

Query  844    GGTACTGCACCTTTCTTCTGGAATTGGGCGATGGTAGCTATGACAACTCTCCTTCCTCCT   903
              ||||||||||||||||||||||||||||||||||||||||||||| |||||||||||||
Sbjct  840    GGTACTGCACCTTTCTTCTGGAATTGGGCGATGGTAGCTATGACAAGTCTCCTTCCTCCT   899
```

FIG. 11B

```
Query   904   GGTATTCTGAGAGACAGAAATAAAATCGGAATGTTGGCAAATTTTGTGTACCCTTCTGTA   963
              |||||||||||||||||||| ||| | || |||||||||||||| |||||||||||||
Sbjct   900   GGTATTCTGAGAGACAGAAATATATTGAAAAGTTGGCAAATTTTGTCTACCCTTCTGTA   959

Query   964   CAAATTTTTGATGGGATTGCAGGAGAATGTCTTGCAATGCGGGTTGATTTAGAGTGCGCA   1023
              ||| ||||||||| |||||||||||||||| || |||||||||||||||| ||||||||
Sbjct   960   CAAGTTTTTGATGGTATTGCAGGAGAATGTCTGCTATGCGGGTTGATTTGGAGTGCGCA   1019

Query   1024  AATGGGCGCAATACTTTTGGTATACTCAGTCATGAACGTCTCTCTGTATTAGTGGGAACT   1083
              ||||||||| |||| || ||||||||||| |||||||||||||||| |||||||||||
Sbjct   1020  AATGGGCGCAACACTTCTGCTATACTCAGTCACGAACGTCTCTCTGAATTAGTGGGAACT   1079

Query   1084  TCAACTGCGGTGTTTGCTATGGCAATTCTTGAAGGAAGTACGCAGCCTGGAGTTTGGTTT   1143
              ||||| |||||||||||| |||||||||||| ||||||||| |||| ||||| |||||||
Sbjct   1080  TCAACCGCGGTGTTTGCTTTGGCAATTCTTGAGGGAAGTACACAGGCTGGTGTTTGGTTT   1139

Query   1144  CCAGAAGAGCCTGGAGGGATTGCAATAAGTGACAGAGAGTTACTTCTACAACGAGCATCA   1203
              |||||||||| | ||||||||| | | ||||||| |||||||| |||||||||||||||
Sbjct   1140  CCAGAAGAGCCCGAGGGGATTGCAGTAGGAGACAGAGAATTACTTCTAAAACGAGCATCA   1199

Query   1204  CAAGGAGCGATTAACTTCATTATGAAGCAGTAGAGTAATAGATTGGATTATTCATTATGT   1263
              |||||||| ||||||||||||||||||||||||| |||||||||||||||||||||||
Sbjct   1200  CAAGGAGCTATTAACTTCATTATGAAGCAGTAGAGCAATAGATTGGATTATTCATTATGT   1259

Query   1264  AGCCAGAATGACATTATTTACATGTAATGTTGCTTCTATGTATCAATAACATA         1317
              |||| ||||| ||||||||||||||||||||| |||||||||||||||||||||
Sbjct   1260  AGCCAAGAATAACATTATTTACATGTAATGTTCCTTCTATGTATCAATAACATA         1313
```

FIG. 12

Comparison of predicted amino acid sequences of *AdKC28* and *AdKC17*

AdKC28(Query) vs. AdKC17 (Sbjct)
Identities = 369/390 (94%), Positives = 377/390 (96%), Gaps = 0/390 (0%)

```
Query   18   VKETNVGSTLASPLNKTQNSRVLVLGGTGKVGGSTALALSKFSPDLRLVIGGRNREKGDA   77
             V ET VG+TL SPLNKTQNSRVLVLGGTGKVGGSTA ALSKFSPDLRLVIGGRNREKGDA
Sbjct   20   VKETTVGNTLVSPLNKTQNSRVLVLGGTGKVGGSTAFALSKFSPDLRLVIGGRNREKGDA   79

Query   78   VVSKLGENSEFVEVNVDSVRSLESALEDVDLVVHAAGPFQQAEKCTVLEAAISTRTAYVD   137
             VVSKLGENSEFVEVNVDS+RSLESA +DVDLVVHAAGPFQQAEKCTVLEAAISTRTAYVD
Sbjct   80   VVSKLGENSEFVEVNVDSMRSLESAFKDVDLVVHAAGPFQQAEKCTVLEAAISTRTAYVD   139

Query   138  VCDNTSYSMQAKSFHDKAVAANVPAITTAGIFPGVSNVIAAELVRSARDENTEPQRLRFS   197
             VCDNTSYSMQAKSFHDKAVAANVPAITTAGIFPGVSNVIAAELVRSARDENTEPQRLRFS
Sbjct   140  VCDNTSYSMQAKSFHDKAVAANVPAITTAGIFPGVSNVIAAELVRSARDENTEPQRLRFS   199

Query   198  YFTAGSGGAGPTSLVTSFLLLGEEVVAYSEGEKVELKPYTGKLNIDFGKGVGKRDVYLWN   257
             YFTAGSGGAGPTSLVTSFLLLGEEVVAYSEGEKVELKPYTGKLNIDFGKGVGKRDVYLWN
Sbjct   200  YFTAGSGGAGPTSLVTSFLLLGEEVVAYSEGEKVELKPYTGKLNIDFGKGVGKRDVYLWN   259

Query   258  LPEVRSGHEILGVPTVSARFGTAPFFWNWAMVAMTTLLPPGILRDRNKIGMLANFVYPSV   317
             LPEVRSGHEILGVPTVSARFGTAPFFWNWAMVAMT+LLPPGILRDRN I  LANFVYPSV
Sbjct   260  LPEVRSGHEILGVPTVSARFGTAPFFWNWAMVAMTSLLPPGILRDRNIIEKLANFVYPSV   319

Query   318  QIFDGIAGECLAMRVDLECANGRNTFGILSHERLSVLVGTSTAVFAMAILEGSTQPGVWF   377
             Q+FDGIAGECLAMRVDLECANGRNT  ILSHERLS LVGTSTAVFA+AILEGSTQ GVWF
Sbjct   320  QVFDGIAGECLAMRVDLECANGRNTSAILSHERLSELVGTSTAVFALAILEGSTQAGVWF   379

Query   378  PEEPGGIAISDRELLLQRASQGAINFIMKQ   407
             PEEP GIA+ DRELLL+RASQGAINFIMKQ
Sbjct   380  PEEPEGIAVGDRELLLKRASQGAINFIMKQ   409
```

BIOCHEMICAL ROUTE TO ASTAXANTHIN

This is a national stage of PCT/US07/009803 filed Apr. 20, 2006 and published in English, claiming benefit of U.S. provisional application No. 60/793,645, filed Apr. 21, 2006, hereby incorporated by reference.

This research was supported in part by the National Science Foundation, Contract No. MCB0316448. The U.S. Government has certain rights in this invention

BACKGROUND OF THE INVENTION

The blood red color, verging on black at the base, displayed by the petals of flowers of *Adonis aestivalis* and *Adonis annua* results from the accumulation of carotenoid pigments (Egger, 1965; Neamtu et al., 1966; Seybold and Goodwin, 1959), predominantly the ketocarotenoid astaxanthin (3,3'-dihydroxy-4,4'-diketo-β,β-carotene; FIG. 1). The biosynthesis of astaxanthin occurs in a number of bacteria and fungi (Goodwin, 1980; Johnson and An, 1991), and in certain unicellular algae (Goodwin, 1980; Grung and Liaaen-Jensen, 1993; Johnson and An, 1991; Orosa et al., 2000). Astaxanthin has been found in a few other plant species (Czeczuga, 1987; Goodwin, 1980), but no other plant produces this ketocarotenoid in as great a quantity as in *Adonis* flowers [ca. 1% of dry weight for the flower petals of *Adonis annua* according to Renstrøm et al., (1981)].

Astaxanthin has found use as a topical antioxidant (in sun blocking lotions, for example) and as an ingredient of human nutritional supplements. See U.S. Pat. No. 6,433,025 to Lorenz. This carotenoid, however, is perhaps best known for providing an attractive orange-red color to the flesh of wild salmon and other fish (Shahidi et al, 1998) and a blue hue (changing to red upon boiling as the proteins that bind astaxanthin are denatured) to the carapace of lobster and of other crustaceans (Chayen et al., 2003; Tanaka et al., 1976).

Fish and crustaceans that are raised in captivity require the addition of astaxanthin to their feed in order to acquire the appropriate coloration. The substantial and expanding market for astaxanthin as a fish feed additive is supplied largely by chemical synthesis, but there is considerable interest in the development of a biological production process to provide an alternative source of this valuable ketocarotenoid. The green alga *Haematococcus pluvialis* (Lorenz and Cysewski, 2000; Orosa et al., 2000) and the fungus *Xanthophyllomyces dendrorhous* (formerly known as *Phaffia rhodozyma*; Johnson, 2003; Visser et al., 2003,) have received the most attention in this regard. See also U.S. Pat. No. 6,413,736 to Jacobson et al., and incorporated by reference herein as if set forth in its entirety. However, the cost of producing astaxanthin in these organisms remains much greater than that for astaxanthin produced by chemical synthesis.

Currently, synthetic astaxanthin is added to feeds prepared for production of salmonids and red sea bream in aquaculture to provide a source of this carotenoid compound. See, for example, U.S. Pat. No. 5,739,006 to Abe et al. In some cases, synthetic canthaxanthin (an oxygenated carotenoid compound that is very closely related to astaxanthin) is used in place of astaxanthin in feeds for salmonids and red sea bream, but this compound does not add the appropriate color to these fishes as efficiently as the naturally predominant astaxanthin.

Recently, attempts have been made, with limited success, to engineer plants for astaxanthin production by introduction of genes from algal and/or bacterial carotenoid pathways (Mann et al., 2000; Ralley et al., 2004; Stålberg et al., 2003). Problems encountered with this strategy include: an incomplete conversion of precursors (i.e. β-carotene and zeaxanthin) into astaxanthin, competition of the introduced bacterial or green algal enzymes with endogenous enzymes that also use β-carotene and/or zeaxanthin as substrates (i.e. zeaxanthin epoxidase), and the accumulation of unwanted intermediates of the pathway (i.e. adonixanthin and adonirubin).

A few attempts have been made to develop and exploit *Adonis aestivalis* as a source of astaxanthin for the pigmentation of fish (Kamata et al., 1990; Rodney, 1995), and this plant is currently grown in China expressly for this purpose. However, despite high concentrations of astaxanthin in the flower petals, a relatively low yield of petal biomass per acre makes *Adonis* a less than ideal vehicle for biological production of this pigment. An understanding of the biosynthetic pathway leading to astaxanthin in *Adonis aestivalis* would enable the pathway to be transferred to other plants, such as marigold, that could provide a much greater yield of carotenoid-containing biomass and, therefore, a much less costly source of natural astaxanthin.

From zeaxanthin (3,3'-dihydroxy-β,β-carotene), a dihydroxy carotenoid present in the green tissues of most higher plants, the formation of astaxanthin requires only that a carbonyl be introduced at the number 4 carbon of each ring (FIG. 1). As a practical matter, the addition of the carbonyl may need to occur prior to hydroxylation of the ring [i.e. β-carotene rather than zeaxanthin would be the substrate for the enzyme, and echinenone (4-keto-β,β-carotene) and canthaxanthin (4,4'-diketo-β,β-carotene) would be the immediate products (Breitenbach et al., 1996; Fraser et al., 1998; Lotan and Hirschberg, 1995)]. Enzymes that catalyze carbonyl addition at the number 4 carbon of carotenoid β-rings have so far been identified in bacteria (De Souza et al., 2002; Harker and Hirschberg, 1999; Misawa et al., 1995a and 1995b), photosynthetic bacteria (Hannibal et al., 2000), cyanobacteria (Fernandez-Gonzalez et at, 1997; Steiger and Sandmann, 2004), and green algae (Kajiwara et al., 1995; Lotan and Hirschberg, 1995). The green algal enzymes that have been characterized are orthologs of those found in bacteria, in photosynthetic bacteria, and in certain of the cyanobacteria, as evidenced by the significant similarity of their amino acid sequences. The "4-ketolase" enzyme of the cyanobacterium *Synechocystis* sp. PCC6803 is distinctly different from these others (Fernandez-Gonzalez et al., 1997). It is related instead to an enzyme that catalyzes an earlier step in the carotenoid pathway of *Synechocystis*: the carotene isomerase (Breitenbach et al., 2001; Masamoto et al., 2001). What appears to be a third type of 4-ketolase enzyme, found in the fungus *Xanthophyllomyces dendrorhous* (*Phaffia rhodozyma*), is related to cytochrome $P_{450}$ enzymes (Hoshino et al., 2002). The activity of this enzyme has not yet been demonstrated directly. The enzyme's putative function as an "astaxanthin synthase" has been attributed on the basis of genetic complementation experiments. The gene encoding this enzyme restores the ability to synthesize astaxanthin in a *X. dendrorhous* mutant that accumulates only β-carotene (Hoshino et al., 2002). Because no mutants have been found that accumulate any of the intermediates between β-carotene and astaxanthin (Visser et al., 2003), it is thought that the product of this gene is responsible for both 3-hydroxylation and 4-keto addition.

The green plant *Adonis aestivalis* synthesizes carotenoids with 4-keto-β-rings via a biochemical pathway unrelated to any yet characterized or described. The present inventor has previously disclosed (U.S. Pat. No. 6,551,807 to Cunningham) two nucleic acid sequences from *Adonis aestivalis* (FIG. 2 and FIG. 3; SEQ ID NO: 1 and SEQ ID NO: 2) that encode enzymes (FIG. 4; SEQ ID NO: 3 and SEQ ID NO: 4) which convert β-carotene into carotenoids with ketocarotenoid-like absorption spectra (i.e. red-shifted and with a diminution of spectral fine structure). More recent work (Cunningham and Gantt, 2005) has demonstrated that the *Adonis aestivalis* "ketolase" enzymes described in this earlier patent (AdKeto1 and AdKeto2) each catalyze two different reactions: a desaturation of carotenoid β-rings at the 3-4 position and a hydroxylation at the number 4 carbon. The inventor now discloses herein the DNA sequence of an *Adonis aestivalis* cDNA that encodes an enzyme, referred to as AdKC28, that works in concert with either one of the two 3,4-desaturase/4-hydroxylase enzymes previously described (AdKeto1 and AdKeto2) to convert β-carotene into astaxanthin.

SUMMARY OF THE INVENTION

There is an increasing demand for biological or "natural" sources of carotenoid pigments for use as food colorants, feed additives, and nutritional supplements. The invention described herein provides the nucleotide sequence of a cDNA (AdKC28) obtained from the flowering plant *Adonis aestivalis*, and entails the use of this cDNA or other nucleotides similar in sequence to this cDNA, together with either one of two *Adonis aestivalis* "ketolase" cDNAs (AdKeto1 and AdKeto2) disclosed in an earlier patent (U.S. Pat. No. 6,551,807 B1), to produce polypeptides that catalyze the conversion of β-carotene into astaxanthin. This invention makes available a new biochemical route, one unrelated to any previously described, that leads to the valuable ketocarotenoid astaxanthin. This new biochemical process provides a number of advantages when compared to the already existing biotechnology.

It is an object of the present invention to provide *Adonis aestivalis* enzymes adapted to function and efficiently produce a substantial quantity of astaxanthin in the context of a plant pathway of carotenoid biosynthesis. The production of astaxanthin in transgenic plants that express these *Adonis aestivalis* enzymes is more likely to proceed efficiently and with high yield of astaxanthin than in those wherein genes encoding bacterial or fungal or green algal enzymes are introduced.

Another object of the present invention is to provide *Adonis aestivalis* genes that produce enzymes having N-terminal sequences needed to target them efficiently to the appropriate membranes within the plastids of plant cells.

Yet another object of the present invention is to provide transgenic plants that are engineered to produce astaxanthin using genes obtained from *Adonis aestivalis*, itself a plant species that may be more readily accepted by consumers than transgenic plants constructed using genes isolated from bacteria or fungi or green algae. In addition, because the target tissues of transformed plants will have an obvious phenotype (a dark red color), it should be possible to select for transgenic plants visually rather than with selectable markers of bacterial origin as is commonly done It is a further object of the present invention to provide an efficient method for production of astaxanthin that requires only two *Adonis aestivalis* gene products to convert β-carotene into astaxanthin not only in a plant plastid, but also within the context of a simple bacterial cell (see Example 1 below). Therefore, the process described in the present invention will function in cells, tissues, organs, and organisms of almost any type, as long as they produce or can be made to produce the requisite substrate, β-carotene.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings.

FIG. 2 displays the nucleotide sequence of the *Adonis aestivalis* cDNA referred to as AdKeto1 (SEQ ID NO: 1)

FIG. 3 displays the nucleotide sequence of the *Adonis aestivalis* cDNA referred to as AdKeto2 (SEQ ID NO: 2)

FIG. 4 shows an alignment of the amino acid sequences (SEQ ID NO: 3 and SEQ ID NO: 4) deduced for polypeptides encoded by *Adonis aestivalis* cDNAs AdKeto1 (SEQ ID NO: 1) (GenBank accession number AY644757) and AdKeto2 (SEQ ID NO: 2) (GenBank accession numbers AY644758 and AY644759). A total of 276 of 306 residues (90.2%) of the overlapping sequences (with no gaps in the alignment) are identical. These residues are shown in white text within a black box.

FIG. 5 displays the nucleotide sequence of the *Adonis aestivalis* cDNA referred to herein as AdKC28 (SEQ ID NO: 5).

FIG. 6 displays the deduced amino acid sequence of the polypeptide (SEQ ID NO: 6) encoded by AdKC28 for bases 13-1233 (SEQ ID NO: 5).

FIG. 7 provides an alignment of the deduced amino acid sequence (SEQ ID NO: 6) of *Adonis aestivalis* cDNA AdKC28 (SEQ ID NO: 5) with that deduced (SEQ ID NO: 7) for an *Arabidopsis thaliana* gene referred to as At1g50450 (GenBank accession number AAM19877.1 and GI:20453277). Residues identical for both sequences are shown in white text within a black box. A total of 256 of 408 residues (62.7%) of the overlapping sequences (with one gap) are identical.

FIG. 9 shows the DNA sequence (SEQ ID NO: 11) for *Adonis aestivalis* cDNA AdKC17.

FIG. 10 is the corresponding amino acid translated sequence (SEQ ID NO: 12) of cDNA AdKC17 for bases 3-1229.

FIGS. 11A and 11B is a comparison of the nucleotide sequences of AdKC28 (SEQ ID NO: 5) and AdKC17 (SEQ ID NO: 11).

FIG. 12 is a comparison of the predicted amino acid sequences of AdKC28 (SEQ ID NO: 6) and AdKC17 (SEQ ID NO: 12).

DETAILED DESCRIPTION AND PREFERRED EMBODIMENTS

Figure 1:
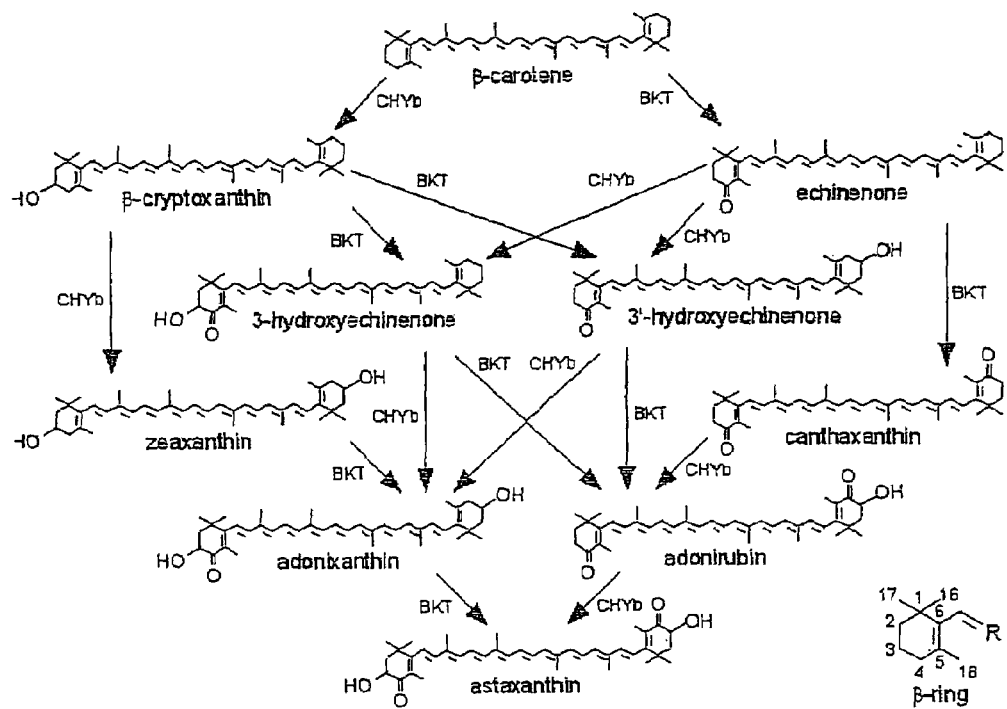
FIG. 1 illustrates the pathway to astaxanthin from β-carotene in green algae and in bacteria. Several routes may be followed, depending on the order of addition of the 3-hydroxyl and 4-keto groups to the two β-rings of the symmetrical substrate β-carotene. Conventional numbering of the carbon atoms of a β-ring is shown at the lower right. Abbreviations: BKT, β-carotene 4-ketolase (Note: while the green algal enzymes are commonly referred to as BKT, the bacterial β-carotene 4-ketolase enzymes are referred to as CrtW); CHYβ, β-carotene 3-hydroxylase (Note: bacterial β-carotene 3-hydroxylase enzymes are referred to as CrtZ).

The present invention is directed to two purified nucleic acid sequences that have all or some substantial portion of the nucleic acid sequence of AdKC28 (SEQ ID NO: 5), or AdKC17 (FIG. 9), and which encodes for a protein having a particular enzymatic activity such that β-carotene is converted into astaxanthin when the polypeptide product of this nucleotide is produced together with the product of one or the other of two previously described nucleic acids (AdKeto1 and AdKeto2; SEQ ID NOS: 1 and 2; U.S. Pat. No. 6,551,807 B1).

The present invention also provides for a purified polypeptide having all or a substantial portion of the amino acid sequence of SEQ ID NO: 6 or FIG. 10. This invention also includes the combination of the nucleic acid of SEQ ID NO: 5, or one which otherwise encodes all or a substantial portion of the polypeptide sequence of SEQ ID NO: 6, together with a nucleic acid that encodes all or a substantial portion of the polypeptide of SEQ ID NO: 3 or that of SEQ ID NO: 4. This invention also includes the combination of a polypeptide with all or a substantial portion of the amino acid sequence of SEQ ID NO: 6, together with a polypeptide with all or a substantial portion of the amino acid sequence of SEQ ID NO: 3 or that of SEQ ID NO: 4.

The nucleic acid sequence of the *Adonis aestivalis* cDNA referred to as AdKC28 (SEQ ID NO: 5) is shown in FIG. 5, and the amino acid sequence deduced for the polypeptide product (SEQ ID NO: 6) of this nucleic acid is displayed in FIG. 6. The nucleic acid sequence of the *Adonis aestivalis* cDNA referred to as AdKC17 is shown in FIG. 9, and the amino acid sequence deduced for the polypeptide product of this nucleic acid is displayed in FIG. 10. No sequence in the GenBank database is more than 70% identical in amino acid sequence to AdKC28. The amino acid sequence deduced for an *Arabidopsis thaliana* gene/cDNA known as At1g50450 is the closest match, with only about 63% identity overall. An alignment of AdKC28 and At1g50450 is shown in FIG. 7. Genes encoding products similar in sequence to AdKC28 (SEQ ID NO: 6) are also present in many other plants (based on a BLAST search of the GenBank EST database), in the green alga *Chlamydomonas reinhardtii* (based on a BLAST search of the JGI *Chlamydomonas reinhardtii* genome database at http://genome.jg-psf.org/chlre2/chlre2.home.html) and in several cyanobacteria (ca. 30% identity for comparisons of the various cyanobacterial gene products with AdKC28). The functions of the plant, algal and cyanobacterial gene products that are similar in sequence to AdKC28 are, as yet, unknown.

An alignment of the amino acid sequences of the products (SEQ ID NO: 3 and SEQ ID NO: 4) of *Adonis aestivalis* cDNAs AdKeto1 and AdKeto2 (SEQ ID NO: 1 and SEQ ID NO: 2) is displayed in FIG. 4. As discussed earlier, these polypeptides, which are about 90% identical in amino acid sequence overall (FIG. 4), exhibit essentially the same enzymatic activity when provided with β-carotene as the substrate, and various truncations, deletions and alterations of the coding region may be made without impairing the catalytic activity. No polypeptides presently in the GenBank database are more than 53% identical to the amino acid sequences of the two AdKeto polypeptides (AdKeto1 and AdKeto2; SEQ ID NO: 3 and SEQ ID NO: 4).

In each case, nucleic acid and amino acid sequence similarity and identity is measured using sequence analysis software, for example, the Sequence Analysis, Gap, or BestFit software packages of the Genetics Computer Group (University of Wis. Biotechnology Center, 1710 University Avenue, Madison, Wis. 53705), MEGAlign (DNAStar, Inc., 1228 S. Park St., Madison, Wis. 53715), or MacVector (Oxford Molecular Group, 2105 S. Bascom Avenue, Suite 200, Campbell, Calif. 95008).

Conservative (i.e. similar) substitutions typically include substitutions within the following groups: glycine and alanine; valine, isoleucine and leucine; aspartic acid, glutamic acid, asparagine and glutamine; serine and threonine; lysine and arginine; and phenylalanine and tyrosine. Substitutions may also be made on the basis of conserved hydrophobicity or hydrophilicity (see Kyte and Doolittle, J. Mol. Biol. 157: 105-132 (1982)), or on the basis of the ability to assume similar polypeptide secondary structure (see Chou and Fasman, Adv. Enzymol. 47: 45-148 (1978)).

The nucleic acid molecules of the present invention are useful for probes, primers, chemical intermediates, and in biological assays. The nucleic acid molecules are useful as hybridization probes for messenger RNA, transcript/cDNA and genomic DNA to isolate full-length cDNA and genomic clones encoding polypeptides similar in sequence to that described in FIG. 6 (SEQ ID NO: 6) and to isolate cDNA and genomic clones that correspond to variants (alleles, orthologs, etc.) producing polypeptides identical or similar in sequence to that shown in FIG. 6.

A probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful for designing primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the polypeptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for constructing transgenic animals expressing all, or a part, of the nucleic acid molecules and polypeptides and are discussed in detail further.

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, or MAC. A vector can be maintained in the host cell as an extrachromosomal element where it replicates and produces additional copies of the nucleic acid molecules. Alternatively, the vector may integrate into the host cell genome and produce additional copies of the nucleic acid molecules when the host cell replicates.

Expression vectors contain cis-acting regulatory regions that are operably linked in the vector to the nucleic acid molecules such that transcription of the nucleic acid molecules is facilitated or allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to facilitate or allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

As described herein, it may be desirable to express the polypeptides as fusion proteins. Accordingly, the invention provides fusion vectors that allow for the production of the peptides. Fusion vectors can increase the expression of a recombinant protein; increase the solubility of the recombinant protein, and aid in the purification of the protein by acting, for example, as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, enterokinase, and the TEV protease. Typical fusion expression vectors include pGEX (Smith et al., Gene 67:31-40 (1988)), pMAL (New England Biolabs, Beverly, Mass.) and pRITS (Pharmacia, Piscataway, N.J.) which fuse glutathione S-transferase (GST), maltose-binding protein, or protein A, respectively, to the target recombinant protein. Examples of suitable inducible non-fusion *E. coli* expression vectors include pTrc (Amann et al., Gene 69:301-315 (1988)) and pET 11d (Studier et al., Gene Expression Technology: Methods in Enzymology 185:60-89 (1990)).

Pharmaceutical and Nutritional Preparations

Dried *Haematococcus* algae, *Phaffia* yeast powder, or synthetic astaxanthin can each be formulated into various food grade oils such as safflower, canola, tocopherols or rice bran and manufactured into gelcaps for convenient ingestion. Alternatively, dried *Haematococcus* algae, *Phaffia* yeast powder, or synthetic astaxanthin can be stabilized by various commercial processes and added directly to foods or beverages.

Thus, the inventor also presents a treatment and method for retarding and prevention of sunburns, and possibly related cancers resulting from long term sunburn damage and a treatment and method of retarding and preventing sunburns by administering a therapeutically effective dose of astaxanthin made using the enzyme derived from the DNA sequence AdKC28.

The astaxanthin made using the enzyme derived from the DNA sequence AdKC28 is preferably administered orally, in doses of between about 1 to about 100 mg per day. Doses of between about 2 to about 10 mg per day are preferable. The dose may be administered to be taken with meals, twice daily.

In addition to an oral administration, a formulation of astaxanthin may also be applied in a cream or injected into the exposed area. Such a dose would also be in the range of about 1 to 100 mg per day.

It is preferable, with an ingestible form of astaxanthin, to begin administering the astaxanthin at least two or three days before sun exposure, and preferably at least a week before exposure, in order to prevent sunburn. However, as seen below in the examples, even ingestion during or after exposure provides beneficial effects. With the topical and injectable treatment, astaxanthin may be administered before, during, or after exposure.

Any and all organisms that synthesize carotenoids are potential candidates for astaxanthin production using the *Adonis aestivalis* cDNAs disclosed and described herein. A number of plants, some fungi and yeasts, and several green algae have been utilized commercially as sources of carotenoid pigments. In these organisms the carotenoids of interest may be accumulated within specific organs or tissues (e.g. the flower petals of marigold, the roots of carrot and the tubers of sweet potato), may be induced under particular environmental conditions or times of development (as in certain species of the green algae *Haematococcus* and *Dunaliella*), or may result from transgenic modification of the host (as in the seeds of canola expressing a bacterial phytoene synthase gene; Ravanello et al., 2003; Shewmaker et al., 1999).

Host systems according to the present invention preferably comprise any organism which is capable of producing carotenoids, or which already produces carotenoids. Such organisms include plants, algae, certain bacteria, cyanobacteria and other photosynthetic bacteria. Transformation of these hosts with vectors according to the present invention can be done using standard techniques. See, for example, Sambrook et al., Molecular Cloning: A Laboratory Manual, Cold Spring Harbor Laboratory, Cold Spring Harbor, N.Y., 1989; Ausubel et al., Current Protocols in Molecular Biology, Greene Publishing and Wiley Interscience, New York, 1991.

The present invention also includes vectors containing the nucleic acids of the invention. Suitable vectors according to the present invention comprise a gene encoding a ketolase enzyme as described above, wherein the gene is operably linked to a suitable promoter. Suitable promoters for the vector can be constructed using techniques well known in the art (see, for example, Sambrook et al., Molecular Cloning: A Laboratory Manual, Cold Spring Harbor Laboratory, Cold Spring Harbor, N.Y., 1989; Ausubel et al., Current Protocols in Molecular Biology, Greene Publishing and Wiley Interscience, New York, 1991). Suitable vectors for eukaryotic expression in plants are described in Fray et al., (1995; Plant J. 8:693-701) and Misawa et al., (1994; Plant J. 6:481-489). Suitable vectors for prokaryotic expression include pACYC184, pUC119, and pBR322 (available from New England BioLabs, Beverly, Mass.) and pTrcHis (Invitrogen) and pET28 (Novagen) and derivatives thereof. The vectors of the present invention can additionally contain regulatory elements such as promoters, repressors, selectable markers such as antibiotic resistance genes, etc., the construction of which is very well known in the art.

For the purpose of astaxanthin production of the present invention, the preferred microbial, fungal, plant and algal hosts for the *Adonis aestivalis* genes are those that produce or can be made to produce a substantial quantity of β-carotene or metabolites thereof. Among the more preferred hosts at this time are: marigold (in the flowers; especially those of mutants or varieties that accumulate predominantly β-carotene), transgenic canola (with carotenoid-accumulating seeds, as in Shewmaker et al., 1999), oil palm (various species of the genus *Elaeis*; the carotenoid-accumulating seeds), carrot (the β-carotene-accumulating root), sweet potato (the β-carotene-rich tubers), maize (the carotenoid-accumulating seeds), tomato (the fruits, especially in varieties or transgenic plants that accumulate largely β-carotene rather than lycopene), and various high β-carotene producing species of the green alga *Dunaliella*.

The genes encoding the *Adonis aestivalis* ketolase enzymes as described above, when cloned into a suitable expression vector, can be produce these enzymes in great quantity in a host cell expression system or to inhibit the production of these enzymes. For example, a vector containing a gene of the invention may be used to increase the amount of ketocarotenoids in an organism and thereby alter the nutritional or commercial value or pharmacology of the organism. A vector containing a gene of the invention may also be used to modify the carotenoid production in an organism.

Methodologies for producing transgenic bacteria, fungi, algae, and plants are widely known and familiar to those skilled in the arts. It is desirable to employ promoters that restrict the expression of the *Adonis aestivalis* genes to the carotenoid-rich tissues or to an appropriate time of development in order to avoid possible adverse effects on yield.

Therefore, the present invention includes a method of producing a ketocarotenoid in a host cell, the method comprising inserting into the host cell a vector comprising a heterologous nucleic acid sequence which encodes for a protein having ketolase enzyme activity and comprises (1) SEQ ID NO: 5 or (2) a sequence which encodes the amino acid sequence of SEQ ID NO: 6, wherein the heterologous nucleic acid sequence is operably linked to a promoter; and expressing the heterologous nucleic acid sequence, thereby producing ketocarotenoid when the appropriate substrate is available.

On the basis of the teachings disclosed here and in an earlier patent (U.S. Pat. No. 6,551,807, hereby incorporated by reference in its entirety as if completely set forth in the specification), one of ordinary skill in the art would be able create nucleotides that encode polypeptides similar in sequence to and with the same catalytic activity as AdKC28, AdKeto1 and AdKeto2. One can isolate such nucleotides from a different accession of *Adonis aestivalis* or from one of the other species of *Adonis* that produce astaxanthin. Alternatively, one skilled in the art can create different nucleotides that would encode the polypeptides of SEQ ID NO: 3, SEQ ID NO: 4 and SEQ ID NO: 6, or polypeptides somewhat different from SEQ ID NO: 3, SEQ ID NO: 4, and SEQ ID NO: 6 but that would retain the catalytic activity of these proteins. Such modifications are well known in genetic engineering. Examples include the introduction of a restriction site, addition of a transit sequence, "conservative" (i.e. similar) substitutions for various amino acids, and alteration of the codon usage so as to be more compatible with transcriptional machinery of the host organism. Therefore, in the context of the present invention, the applicant discloses and claims nucleotides that encode polypeptides that are >70% identical to, in whole or in large part, and exhibit the catalytic function of those polypeptides of SEQ ID NO: 3, SEQ ID NO: 4 and SEQ ID NO: 6. Such claims would not include or encompass any other nucleotides or polypeptides that are currently available in the GenBank databases.

The term "modifying the production" means that the amount of carotenoids produced can be enhanced, reduced, or left the same, as compared to an untransformed host cell. In accordance with one embodiment of the present invention, the composition of the carotenoids (i.e. the identities and relative amounts of the specific carotenoids produced) may be altered, and this change in composition may result in either a net gain, net loss, or no net change in the amount of carotenoids produced in the cell.

It is expressly stated that the numbering of the elements of the sequences (on the one hand nucleic acid sequences and on the other amino acid sequences) shall not be understood as a fixed or limiting definition. The numbering shall merely provide the information of the positions of the sequence elements to each other in relative terms and is therefore a reference.

The term "derivative" means, within the context of the present invention, that the sequences of these molecules differ from the sequences of the nucleic acid molecules according to the invention or to be suitably employed in accordance with the invention in one or more positions and exhibit a high degree of homology to these sequences. Homology in the present context means a sequence identity of at least 60%, preferably over 70%, and especially preferably over 85%, in particular over 90% and very especially preferably over 95%. The deviations relative to the nucleic acid molecules according to the invention or to the nucleic acid molecules to be suitably employed in accordance with the invention may have originated by means of one or more deletions, substitutions, insertions (addition) or recombinations.

Furthermore, homology means that a functional and/or structural equivalence exits between the nucleic acid molecules in question and the proteins encoded by them. The nucleic acid molecules which are homologous to the molecules according to the invention or to the molecules to be suitably employed in accordance with the invention and which constitute derivatives of these molecules are, as a rule, variations of these molecules which constitute modifications which exert the same, a virtually identical or a similar biological function. They may be naturally occurring variations, for example sequences from other plant species, or mutations, it being possible for these mutations to have occurred naturally or to have been introduced by directed or random mutagenesis. The variations may further be synthetic sequences. The allelic variants may be naturally occurring variants or else synthetic variants or variants generated by recombinant DNA technology.

The term "part" regarding the nucleic acid molecule encoding an AdKC28 protein according to this invention encompasses a poly- or oligonucleotide consisting of about at least 30-99, preferably at least 100, more preferably at least 200, in particular at least 300, and most preferably at least 400 of the nucleotides of the nucleic acid molecule encoding an AdKC28 protein or derivative thereof according to the invention. The term "part" is not limited to portions of the nucleic acid molecules which are long enough to encode a functionally active portion of the AdKC28 protein as described.

Having generally described this invention, a further understanding can be obtained by reference to the following specific example which is provided herein for the purpose of illustration only. It is not intended that this example be limiting.

EXAMPLE 1

Production of Astaxanthin in the Bacterium *Escherichia coli*: a Case Study

A strain of the common laboratory bacterium *E. coli* was engineered to produce the carotenoid β-carotene by introduction of a plasmid (pAC-BETA) containing the requisite genes from the bacterium *Erwinia herbicola* (Cunningham et al., 1996). Introduction of a second plasmid containing either the *Adonis aestivalis* DNA sequence AdKeto1 or AdKeto2 (SEQ ID NO: 1 or SEQ ID NO: 2; in plasmid pAdKeto1 or plasmid pAdKeto2) resulted in the conversion of β-carotene into several other carotenoids that contain β-rings with a desaturation at the 3-4 position and/or an hydroxyl group at the number 4 carbon (Cunningham and Gantt, 2005). Addition of a third plasmid, containing the *Adonis aestivalis* nucleotide sequence of AdKC28 (SEQ ID NO: 5) resulted in the synthesis and accumulation, predominantly, of the ketocarotenoid astaxanthin. Absent the second plasmid that contained either AdKeto1 or AdKeto2, the introduction of the plasmid containing the *Adonis aestivalis* DNA sequence AdKC28 into the β-carotene accumulating *E. coli* strain did not alter the carotenoid content: β-carotene remained the predominant pigment.

Two different versions of the third plasmid were used in the above experiments, with each resulting in the accumulation of astaxanthin in good yield. In one plasmid the AdKC28 cDNA (SEQ ID NO: 5) was fused in frame to a portion of a gene encoding the N terminus of a polypeptide encoded by the lacZ gene (in plasmid vector pBluescript SK-; from Stratagene Cloning Systems). The amino acid sequence of the fusion protein specified by this chimerical gene consisted of the full length coding region of AdKC28 (SEQ ID NO: 5; encoding the amino acid sequence of SEQ ID NO: 6) with additional N terminal sequence specified by lacZ and by the 5' untranslated region of AdKC28 (SEQ ID NO: 8; MTMITPSSKLTLTKGNK-SWSSTAVAAALELVDPPGCRNSHEEEHY).

A second version of the plasmid containing AdKC28 was constructed so as to produce the authentic full length polypeptide (SEQ ID NO: 6) under control of the tightly-regulated bacterial araBAD promoter. The coding region of AdKC28 was amplified by PCR using oligonucleotide primers AdKC28Nco-N (CACACCATGGCTCCTGTTCTC-CTTG) (SEQ ID NO: 9) and AdKC28-C (CTGGGCTACAT-AATGAATAATCCAATC) (SEQ ID NO: 10), and the PCR product was digested with the appropriate restriction enzymes and ligated in the NcoI and XhoI sites of plasmid pBAD/HisB (Invitrogen). Biosynthesis of astaxanthin with this plasmid (in *E. coli* cultures also containing the plasmids pAC-BETA and pAdKeto1 or pAdKeto2) occurred only when arabinose was added to induce expression of AdKC28 from the araBAD promoter.

Figure 8:
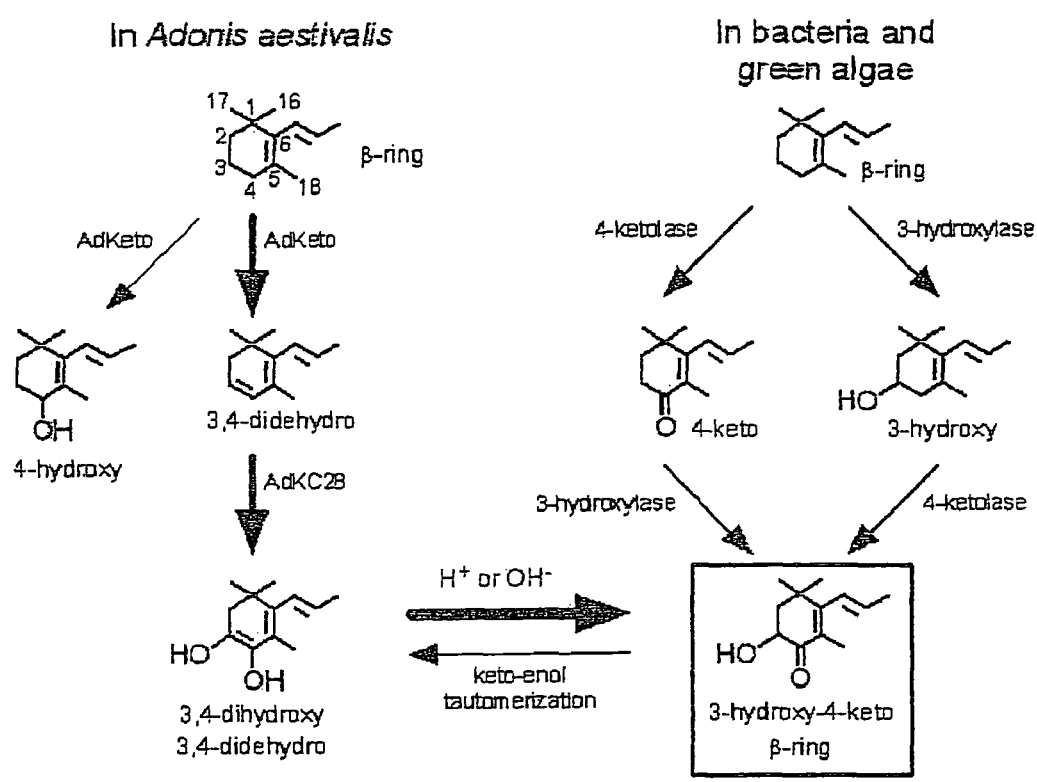
FIG. 8 depicts the biosynthetic pathway leading to a 3-hydroxy-4-keto-β-ring as catalyzed by *Adonis aestivalis* gene product AdKeto1 (or AdKeto2) together with AdKC28. The quite different pathway used by bacteria and green algae is also shown for comparison.

From the above results it can be deduced that, unexpectedly and in contrast to the pathways of bacteria and green algae, the route to carotenoids with 3-hydroxy-4-keto-β-rings in *Adonis aestivalis* does not proceed via either a 3-hydroxy-β ring or a 4-keto-β ring. The sequence of reactions of the present invention (FIG. 8) includes first a desaturation of the β-ring at the 3,4 position (a reaction catalyzed by the AdKeto1 and AdKeto2 "ketolase" enzymes; Cunningham and Gantt, 2005). This reaction is then followed by a dihydroxylation at the number 3 and 4 carbons (a reaction catalyzed by the product of *Adonis aestivalis* cDNA AdKC28), with the 3,4-desaturation either retained or reintroduced by AdKeto1 or AdKeto2. The 3,4-didehydro-3,4-dihydroxy-β-ring thereby produced will spontaneously be converted to a 3-hydroxy-4-keto-β-ring as a consequence of a keto-enol tautomerization.

The data obtained with β-carotene-accumulating *E. coli* clearly demonstrate that the products of two cDNAs derived from mRNA isolated from a flowering plant, *Adonis aestivalis*, are sufficient to convert β-carotene into the valuable keto-carotenoid astaxanthin in the context of a simple bacterial cell. The same two gene products, therefore, should prove sufficient to convert β-carotene into astaxanthin in a wide variety of host organisms, both prokaryotic and eukaryotic, and both photosynthetic and nonphotosynthetic.

Having described the invention, many modifications thereto will become apparent to those skilled in the art to which it pertains without deviation from the spirit of the invention as defined by the scope of the appended claims.

References

The references cited in the above specification, along with the following references, are incorporated by reference in their entireties as if fully set forth in the specification:

Breitenbach, J., Misawa, N., Kajiwara, S. and Sandmann, G. (1996) Expression in *Escherichia coli* and properties of the carotene ketolase from *Haematococcus pluvialis*. FEMS Microbiol. Lett. 140, 241-246.

Breitenbach, J., Vioque, A. and Sandmann, G. (2001) Gene sll0033 from *Synechocystis* 6803 encodes a carotene isomerase involved in the biosynthesis of all-E lycopene. Z. Naturforsch. [C]. 56, 915-917.

Chayen, N. E., Cianci, M., Grossmann, J. G., Habash, J., Helliwell, J. R., Nneji, G. A., Raftery, J., Rizkallah, P. J. and Zagalsky, P. F. (2003) Unravelling the structural chemistry of the colouration mechanism in lobster shell. *Acta Crystallographica* D. Biological Crystallography 59, 2072-2082.

Choi S.-K., Nishida, Y., Matsuda, S., Adachi, K., Kasai, H., Peng, X., Komemushi, S., Miki, W. and Misawa, N. (2005) Characterization of β-carotene ketolases, CrtW, from marine bacteria by complementation analysis in *Escherichia coli*. Mar. Biotechnol. July 5; [Epub ahead of print].

Cunningham, F. X., Jr. and E. Gantt (2005) A study in scarlet: enzymes of ketocarotenoid biosynthesis in the flowers of *Adonis aestivalis*. Plant J. 41, 478-92.

Cunningham, F. X. Jr., Pogson, B., Sun, Z., McDonald, K. A., DellaPenna, D. and Gantt, E. (1996) Functional analysis of the beta and epsilon lycopene cyclase enzymes of *Arabidopsis* reveals a mechanism for control of cyclic carotenoid formation. Plant Cell 8, 1613-1626.

Czeczuga, B. (1987) Ketocarotenoids—autumn carotenoids in *Metasequoia glyptostroboides*. Biochem. Syst. Ecol. 15, 303-306.

De Souza, M. L., Kollmann, S. R. and Schroeder, W. A. (2002) *Carotenoid Biosynthesis*. International patent application PCT WO/02/079395-B.

Egger, K. (1965) Die Ketocarotinoide in *Adonis annua* L. Phytochemistry 4, 609-618.

Fernandez-Gonzalez, B. F., Sandmann, G. and Vioque, A. (1997) A new type of asymmetrically acting beta-carotene ketolase is required for the synthesis of echinenone in the cyanobacterium *Synechocystis* sp. PCC 6803. J. Biol. Chem. 272, 9728-9733.

Fraser, P. D., Shimada, H., and Misawa, N. (1998) Enzymic confirmation of reactions involved in routes to astaxanthin formation, elucidated using a direct substrate in vitro assay. Eur. J. Biochem. 252, 229-236.

Goodwin, T. W. (1980) *The Biochemistry of the Carotenoids* $2^{nd}$ edn, Vol. 1. London: Chapman and Hall.

Grung, M. and Liaaen-Jensen, S. (1993) Algal carotenoids 52; secondary carotenoids of algae 3; carotenoids in a natural bloom of *Euglena sanguinea*. Biochem. Syst. Ecol. 21, 757-763.

Hannibal, L., Lorquin, J., D'Ortoli, N. A., Garcia, N., Chaintreuil, C., Masson-Boivin, C., Dreyfus, B. and Giraud, E. (2000) Isolation and characterization of canthaxanthin biosynthesis genes from the photosynthetic bacterium *Bradyrhizobium* sp. Strain ORS278. J. Bacteriol. 182, 3850-3853.

Harker, M. and Hirschberg, J. (1999) Carotenoid biosynthesis genes in the bacterium *Paracoccus marcusii* MH1, unpublished. GenBank Accession Number Y15112.

Hoshino, T., Kazuyuki, O. and Setoguchi, Y. (2002) *Astaxanthin synthase*. U.S. Pat. No. 6,365,386 B1.

Johnson, E. A. (2003) *Phaffia rhodozyma*: colorful odyssey. Int. Microbiol. 6, 169-174.

Johnson, E. A. and An, G. H. (1991) Astaxanthin from microbial sources. Crit. Rev. Biotechnol. 11, 297-326.

Kajiwara, S., Kakizono, T., Saito, T., Kondo, K., Ohtani, T., Nishio, N., Nagai, S. and Misawa, N. (1995) Isolation and functional identification of a novel cDNA for astaxanthin biosynthesis from *Haematococcus pluvialis*, and astaxanthin synthesis in *Escherichia coli*. Plant Mol. Biol. 29, 343-352.

Kamata, T., Tanaka, Y., Yamada, S. and Simpson K. L. (1990) Study of carotenoid composition and fatty-acids of astaxanthin diester in rainbow-trout salmo-gairdneri fed the *Adonis* extract. Nippon Suisan Gakkaishi 56, 789-794.

Lorenz, R. T. and Cysewski, G. R. (2000) Commercial potential for *Haematococcus* microalgae as a natural source of astaxanthin. Trends Biotechnol. 18, 160-167.

Lotan, T. and Hirschberg, J. (1995) Cloning and expression in *Escherichia coli* of the gene encoding beta-C-4-oxygenase, that converts beta-carotene to the ketocarotenoid canthaxanthin in *Haematococcus pluvialis*. *FEBS Lett.* 364, 125-128.

Mann, V., Harker, M., Pecker, I. and Hirschberg, J. (2000) Metabolic engineering of astaxanthin production in tobacco flowers. *Nat. Biotechnol.* 18, 888-892.

Masamoto, K., Wada, H., Kaneko, T. and Takaichi, S. (2001) Identification of a gene required for cis-to-trans carotene isomerization in carotenogenesis of the cyanobacterium *Synechocystis* sp. PCC 6803. *Plant Cell Physiol.* 42, 1398-1402.

Misawa, N., Satomi, Y., Kondo, K., Yokoyama, A., Kajiwara, S., Saito, T., Ohtani, T. and Mild, W. (1995a) Structure and functional analysis of a marine bacterial carotenoid biosynthesis gene cluster and astaxanthin biosynthetic pathway proposed at the gene level. *J. Bacteriol.* 177, 6575-658418.

Misawa, N., Kajiwara, S., Kondo, K., Yokoyama, A., Satomi, Y., Saito, T., Miki, W. and Ohtani, T. (1995b) Canthaxanthin biosynthesis by the conversion of methylene to keto groups in a hydrocarbon beta-carotene by a single gene. *Biochem. Biophys. Res. Commun.* 209, 867-876.

Neamtu, G., Tamas, V. and Bodea, C. (1966) Die carotinoide aus Einigen *Adonis*-arten. *Rev. Roum. Biochem.* 3, 305-310.

Orosa, M., Torres, E., Fidalgo, P. and Abalde, J. (2000) Production and analysis of secondary carotenoids in green algae. *J. Appl. Phycol.* 12, 553-556.

Raney, L., Enfissi, Misawa, N., Schuch, W., Bramley, P. M. and Fraser, P. D. (2004) Metabolic engineering of ketocarotenoid formation in higher plants. *Plant J* 39, 477-486.

Ravanello, M. P., Ke, D., Alvarez, J., Huang, B. and Shewmaker, C. K. (2003) Coordinate expression of multiple bacterial carotenoid genes in canola leading to altered carotenoid production. *Metabolic Eng.* 5, 255-263.

Renstrom, B., Berger, H. and Liaaen-Jensen, S. (1981) Esterified, optically pure (3S, 3'S)-astaxanthin from flowers of *Adonis annua*. *Biochem. Syst. Ecol.* 9, 249-250.

Rodney, M. (1995) Astaxanthin from flowers of the genus *Adonis*. U.S. Pat. No. 5,453,565.

Seybold, A. and Goodwin, T. W. (1959) Occurrence of astaxanthin in the flower petals of *Adonis annua* L. *Nature* 184, 1714-1715.

Shahidi, F., Metusalach and Brown, J. A. (1998) Carotenoid pigments in seafoods and aquaculture. *Crit. Rev. Food Sci. Nutrition* 38, 1-67.

Shewmaker, C. K., Sheehy, J. A., Daley, M., Colburn, S. and Ke, D. Y. (1999) Seed-specific overexpression of phytoene synthase: increase in carotenoids and other metabolic effects. *Plant J.* 20, 401-412.

Stålberg, K., Lindgren, 0., Ek, B. and Høglund, A.-S. (2003) Synthesis of ketocarotenoids in the seed of *Arabidopsis thaliana*. *Plant J.* 36, 771-779.

Steiger, S. and Sandmann, G. (2004) Cloning of two carotenoid ketolase genes from *Nostoc punctiforme* for the heterologous production of canthaxanthin and astaxanthin. *Biotechnol. Lett.* 26, 813-817.

Tanaka, Y., Matsuguchi, H., Katayama, T., Simpson, K. L. and Chichester, C. O. (1976) The biosynthesis of astaxanthin-XVI. The carotenoids in Crustacea. *Comp. Biochem. Physiol.* B. 54, 391-393.

Visser, H., van Ooyen, A. J. J. and Verdoes, J. C. (2003) Metabolic engineering of the astaxanthin-biosynthetic pathway of *Xanthophyllomyces dendrorhous*. *FEMS Yeast Res.* 4, 221-231.

The invention claimed is:

1. A purified nucleic acid sequence comprising the nucleotide sequence of SEQ ID NO: 5 or SEQ ID NO: 11.

2. An isolated polypeptide encoded by nucleotide sequence of claim 1.

3. The polypeptide of claim 2 comprising the amino acid sequence of SEQ ID NO: 6 or SEQ ID NO: 12.

4. The purified nucleic acid sequence of claim 1, which encodes a polypeptide that works in conjunction with AdKeto 1 or AdKeto2 to convert β-carotene into astaxanthin.

5. A purified nucleic acid sequence which encodes a polypeptide that is 90% or more identical in amino acid sequence to SEQ ID NO: 6 or SEQ ID NO: 12, wherein the polypeptide works in conjunction with AdKeto 1 or AdKeto2 to convert β-carotene into astaxanthin.

6. A purified nucleic acid sequence which encodes a polypeptide that is more than 85% identical in amino acid sequence to SEQ ID NO: 6 or SEQ ID NO: 12, wherein the polypeptide works in conjunction with AdKeto1 or AdKeto2 to convert β-carotene into astaxanthin.

7. A vector comprising the nucleic acid sequence of claim 4.

8. A vector comprising the nucleic acid sequence of claim 5.

9. A vector comprising the nucleic acid sequence of claim 6.

10. A purified polypeptide comprising the amino acid sequence of SEQ ID NO: 6 or SEQ ID NO: 12, wherein the polypeptide works in conjunction with AdKeto1 or AdKeto2 to convert β-carotene into astaxanthin.

11. A purified polypeptide comprising an amino acid sequence that is 90% or more identical in amino acid sequence to SEQ ID NO: 6 or SEQ ID NO: 12, wherein the polypeptide works in conjunction with AdKeto1 or AdKeto2 to convert β-carotene into astaxanthin.

12. A purified polypeptide comprising an amino acid sequence that is more than 85% identical in amino acid sequence to SEQ ID NO: 6 or SEQ ID NO: 12, wherein the polypeptide works in conjunction with AdKeto1 or AdKeto2 to convert β-carotene into astaxanthin.

13. A recombinant, double-stranded DNA molecule comprising:
   a) a promoter functional in plant cells, and
   b) a DNA sequence having at least 80% identity with the coding region of SEQ ID NO: 5 or SEQ ID NO: 11, wherein the DNA sequence is operatively linked to the promoter in sense orientation, encoding for a protein having enzyme activity such that, in conjunction with the product of AdKeto1 or AdKeto2, β-carotene is converted into astaxanthin.

14. A prokaryotic host organism comprising the DNA molecule of claim 13, wherein the prokaryotic organism is *Escherichia coli*.

15. A recombinant, double-stranded DNA molecule comprising:
   a) a promoter functional in plant cells, and
   b) a DNA sequence comprising a sequence which hybridizes with the coding region of SEQ ID NO: 5 or SEQ ID NO: 11, under conditions wherein sodium chloride concentrations are between about 0.02 M to about 0.15 M, and temperatures range from about 50° C. to about 70° C., wherein the DNA sequence is operatively linked to the promoter in sense orientation, encoding for a protein having enzyme activity such that, in conjunction with the product of AdKeto1 or AdKeto2, β-carotene is converted into astaxanthin.

16. The DNA molecule according to claim 13, wherein the DNA sequence comprises SEQ ID NO: 5 or SEQ ID NO: 11.

17. A recombinant, double-stranded DNA molecule comprising:
   a) a promoter functional in plant cells, and
   b) a DNA sequence comprising the coding region of the nucleotide sequence depicted as SEQ ID NO: 5 or SEQ ID NO: 11, or a nucleotide sequence that encodes the polypeptide encoded by SEQ ID NO: 5 or SEQ ID NO: 11, wherein the DNA sequence is operatively linked to the promoter in sense orientation, encoding for a protein having enzyme activity such that, in conjunction with the product of AdKeto1 or AdKeto2, β-carotene is converted into astaxanthin.

18. A transgenic plant cell comprising a recombinant DNA molecule according to claim 13.

19. A transgenic plant comprising plant cells according to claim 18.

20. A vector which comprises the nucleic acid sequence of SEQ ID NO: 5 or SEQ ID NO: 11, wherein the nucleic acid sequence is operably linked to a promoter.

21. A host cell which is transformed with the vector of claim 20.

22. The host cell of claim 21, wherein the host cell is selected from the group consisting of a bacterial cell, an algal cell, a plant cell, and an animal cell.

23. The host cell of claim 21, wherein the host cell is a photosynthetic cell.

24. The host cell of claim 21, wherein the host cell contains a ketocarotenoid.

25. The host cell of claim 21, wherein the host cell contains modified levels of carotenoids, relative to an untransformed host cell.

26. A method of producing astaxanthin and other carotenoids with 3-hydroxy-4-keto-β-rings in a host cell, the method comprising inserting into the host cell nucleic acid sequences that encode polypeptides that are more than 85% identical in sequence to AdKC28 (SEQ ID NO: 6) and/or AdKC17 (SEQ ID NO: 12) and AdKeto1 (SEQ ID NO: 3) or AdKeto2 (SEQ ID NO: 4).

27. The method of claim 26, wherein the nucleotide sequences encode polypeptides that are 90% or more identical in sequence to SEQ ID NO: 6 and/or SEQ ID NO: 12 and SEQ ID NO: 3 or SEQ ID NO: 4.

28. The method of claim 26, wherein the nucleotide sequences encode SEQ ID NO: 6 and/or SEQ ID NO: 12 and SEQ ID NO: 3 or SEQ ID NO: 4.

29. The method of claim 26, wherein the host cell is a bacterium, an archaea, an alga, a yeast, a fungus, a plant, or an animal.

30. The method of claim 27, wherein the host cell is a bacterium, an archaea, an alga, a yeast, a fungus, a plant, or an animal.

31. The method of claim 28, wherein the host cell is a bacterium, an archaea, an alga, a yeast, a fungus, a plant, or an animal.

32. A purified nucleic acid sequence comprising the nucleotide sequence of SEQ ID NO: 11.

33. An isolated polypeptide encoded by the nucleotide sequence of claim 32.

34. An isolated polypeptide comprising the amino acid sequence of SEQ ID NO: 12.

\* \* \* \* \*

SEQUENCE LISTING

```
<160> NUMBER OF SEQ ID NOS: 16

<210> SEQ ID NO 1
<211> LENGTH: 1176
<212> TYPE: DNA
<213> ORGANISM: Adonis aestivalis

<400> SEQUENCE: 1
agcaatctca gtgttcagta caagttattc tttccacaag aatctcttgt tgcactcaaa      60
acaagacatt ctcaaccgcc catgtttgct cttctctcca gttgtggtgg agtcgcctat     120
gagaaagaaa aagacacatc gtgctgcatg tatctgctct gttgcagaga gaacaaggaa     180
ccttgatatt cctcaaattg aagaagagga agagaacgag gaagaactaa tagaacagac     240
ggattctggc ataattcata taaagaaaac gctaggggggg aaacaatcaa gacggtccac     300
tggctccatt gtcgcacccg tatcttgtct tgggatcctt tcaatgatcg gacctgctgt     360
ttacttcaag ttttcacggc taatggagtg tggagatatt cctgtcgcag aaatggggat     420
tacgtttgcc gcctttgttg ctgctgcgat tggcacggaa tttttgtcag gatgggttca     480
caaagaactc tggcacgatt ctttgtggta cattcacaag tctcaccata ggtcacgaaa     540
aggccgcttc gagttcaatg atgtgtttgc tattattaac gcgcttcctg ctattgctct     600
tatcaattat ggattctcaa atgaaggcct ccttcctgga gcctgctttg gtaccggtct     660
tggaacgaca gtctgtggca tggcttacat ttttcttcac aatggccttt cacaccgaag     720
gttcccagta gggcttattg caaacgtccc ttatttccac aagctggctg cagctcacca     780
```

```
aatccatcac tcaggaaaat ttcagggtgt accatttggc ctgttccttg acccccagga      840
attggaagaa gtaagaggag gcactgaaga attggagagg gtgatcagtc gtacagctaa      900
acgaacgcaa tcatctacat gaatcaactc ttttacattt atgaggtttt agtttatcgg      960
tgttacaagt cacacatttg tgtcgttgta gtaattcaaa gttaccatac tcttttttag     1020
aatttttttt tgatgtatag gtcgcggagt tacggttaca aaggccaaat ctattgttgt     1080
ggaattccat tattaaaaat aaaaattaga gtttgtagtt ttatctggtg atcaatatca     1140
atatatatta attaaagcaa aaaaaaaaaa aaaaaa                                1176

<210> SEQ ID NO 2
<211> LENGTH: 1120
<212> TYPE: DNA
<213> ORGANISM: Adonis aestivalis

<400> SEQUENCE: 2
atggcagcag caatttcagt gttcagttca ggttattctt tctacaagaa tctcttgttg       60
gactcaaaac caaatattct caaaccccca tgcctgctat tctctccagt tgtgatcatg      120
tcgcctatga gaaagaaaaa gaaacatggt gatccatgta tctgctccgt tgcagggaga      180
acaaggaacc ttgatattcc tcaaattgaa gaagaggaag agaatgtgga agaactaata      240
gaacagaccg attctgacat agtgcatata aagaaaacac taggggggaa caatcaaaa       300 cggcccactg gctccattgt cgcacccgta tcttgtcttg ggatcctttc aatgattgga      360
cctgctgttt acttcaagtt ttcacggcta atggagggtg gagatatacc tgtagcagaa      420
atggggatta cgtttgccac ctttgttgct gctgctgttg gcacggagtt tttgtcagca      480
tgggttcaca agaactctg gcacgagtct ttgtggtaca ttcacaagtc tcaccatcgg       540
tcacgaaaag gccgcttcga gttcaatgat gtgtttgcta ttattaacgc gcttcccgct      600
attgctctta tcaattatgg attctccaat gaaggcctcc ttcctggagc gtgctttggt      660
gtcggtcttg gaacaacagt ctgtggtatg gcttacattt tccttcacaa tggcctatca      720
caccgaaggt tcccagtatg gcttattgcg aacgtccctt atttccacaa gctggctgca      780
gctcaccaaa tacaccactc aggaaaattt cagggtgtac catttggcct gttccttgga      840
cccaaggaat tggaagaagt aagaggaggc actgaagagt tggagagggt aatcagtcgt      900
acaactaaac gaacgcaacc atctacctga atcaattttt ttacatatat aaggttttag      960
tttatcggtg ttataaaatc acacatccgt atcgttttag taagtcaaag ttaagatact     1020
tccttcttag aatattttt gatgtatagg tcgcggatat actgttacac tattcgttgt      1080
ggaattccat tataaaaaaa taaaaaaaaa aaaaaaaaa                             1120

<210> SEQ ID NO 3
<211> LENGTH: 306
<212> TYPE: PRT
<213> ORGANISM: Adonis aestivalis

<400> SEQUENCE: 3

Ala Ile Ser Val Phe Ser Thr Ser Tyr Ser Phe His Lys Asn Leu Leu
 1               5                  10                  15

Leu His Ser Lys Gln Asp Ile Leu Asn Arg Pro Cys Leu Leu Phe Ser
            20                  25                  30

Pro Val Val Glu Ser Pro Met Arg Lys Lys Thr His Arg Ala
        35                  40                  45

Ala Cys Ile Cys Ser Val Ala Glu Arg Thr Arg Asn Leu Asp Ile Pro
    50                  55                  60
```

-continued

```
Gln Ile Glu Glu Glu Glu Asn Glu Glu Leu Ile Glu Gln Thr
 65                  70                  75                  80

Asp Ser Gly Ile Ile His Ile Lys Lys Thr Leu Gly Gly Lys Gln Ser
                 85                  90                  95

Arg Arg Ser Thr Gly Ser Ile Val Ala Pro Val Ser Cys Leu Gly Ile
            100                 105                 110

Leu Ser Met Ile Gly Pro Ala Val Tyr Phe Lys Phe Ser Arg Leu Met
        115                 120                 125

Glu Cys Gly Asp Ile Pro Val Ala Glu Met Gly Ile Thr Phe Ala Ala
130                 135                 140

Phe Val Ala Ala Ile Gly Thr Glu Phe Leu Ser Gly Trp Val His
145                 150                 155                 160

Lys Glu Leu Trp His Asp Ser Leu Trp Tyr Ile His Lys Ser His His
                165                 170                 175

Arg Ser Arg Lys Gly Arg Phe Glu Phe Asn Asp Val Phe Ala Ile Ile
            180                 185                 190

Asn Ala Leu Pro Ala Ile Ala Leu Ile Asn Tyr Gly Phe Ser Asn Glu
        195                 200                 205

Gly Leu Leu Pro Gly Ala Cys Phe Gly Thr Gly Leu Gly Thr Thr Val
    210                 215                 220

Cys Gly Met Ala Tyr Ile Phe Leu His Asn Gly Leu Ser His Arg Arg
225                 230                 235                 240

Phe Pro Val Gly Leu Ile Ala Asn Val Pro Tyr Phe His Lys Leu Ala
                245                 250                 255

Ala Ala His Gln Ile His His Ser Gly Lys Phe Gln Gly Val Pro Phe
            260                 265                 270

Gly Leu Phe Leu Gly Pro Gln Glu Leu Glu Glu Val Arg Gly Gly Thr
        275                 280                 285

Glu Glu Leu Glu Arg Val Ile Ser Arg Thr Ala Lys Arg Thr Gln Ser
    290                 295                 300

Ser Thr
305

<210> SEQ ID NO 4
<211> LENGTH: 309
<212> TYPE: PRT
<213> ORGANISM: Adonis aestivalis

<400> SEQUENCE: 4

Met Ala Ala Ala Ile Ser Val Phe Ser Ser Gly Tyr Ser Phe Tyr Lys
  1               5                  10                  15

Asn Leu Leu Leu Asp Ser Lys Pro Asn Ile Leu Lys Pro Pro Cys Leu
                 20                  25                  30

Leu Phe Ser Pro Val Val Ile Met Ser Pro Met Arg Lys Lys Lys Lys
             35                  40                  45

His Gly Asp Pro Cys Ile Cys Ser Val Ala Gly Arg Thr Arg Asn Leu
         50                  55                  60

Asp Ile Pro Gln Ile Glu Glu Glu Glu Asn Val Glu Glu Leu Ile
 65                  70                  75                  80

Glu Gln Thr Asp Ser Asp Ile Val His Ile Lys Lys Thr Leu Gly Gly
                 85                  90                  95

Lys Gln Ser Lys Arg Pro Thr Gly Ser Ile Val Ala Pro Val Ser Cys
            100                 105                 110

Leu Gly Ile Leu Ser Met Ile Gly Pro Ala Val Tyr Phe Lys Phe Ser
        115                 120                 125
```

```
Arg Leu Met Glu Gly Gly Asp Ile Pro Val Ala Glu Met Gly Ile Thr
    130                 135                 140

Phe Ala Thr Phe Val Ala Ala Val Gly Thr Glu Phe Leu Ser Ala
145                 150                 155                 160

Trp Val His Lys Glu Leu Trp His Glu Ser Leu Trp Tyr Ile His Lys
                165                 170                 175

Ser His His Arg Ser Arg Lys Gly Arg Phe Glu Phe Asn Asp Val Phe
            180                 185                 190

Ala Ile Ile Asn Ala Leu Pro Ala Ile Ala Leu Ile Asn Tyr Gly Phe
        195                 200                 205

Ser Asn Glu Gly Leu Leu Pro Gly Ala Cys Phe Gly Val Gly Leu Gly
    210                 215                 220

Thr Thr Val Cys Gly Met Ala Tyr Ile Phe Leu His Asn Gly Leu Ser
225                 230                 235                 240

His Arg Arg Phe Pro Val Trp Leu Ile Ala Asn Val Pro Tyr Phe His
                245                 250                 255

Lys Leu Ala Ala Ala His Gln Ile His His Ser Gly Lys Phe Gln Gly
            260                 265                 270

Val Pro Phe Gly Leu Phe Leu Gly Pro Lys Glu Leu Glu Glu Val Arg
        275                 280                 285

Gly Gly Thr Glu Glu Leu Glu Arg Val Ile Ser Arg Thr Thr Lys Arg
    290                 295                 300

Thr Gln Pro Ser Thr
305

<210> SEQ ID NO 5
<211> LENGTH: 1387
<212> TYPE: DNA
<213> ORGANISM: Adonis aestivalis

<400> SEQUENCE: 5
gaagaacatt acatggctcc tgttctcctt ggattgaaac caactctctc cactggaagc      60
gtcgtcaaag agactaatgt aggaagcaca cttgctagtc cccttaacaa acccagaat     120 tcaagggttt tggttttggg cggaacaggg aaggtcggtg gttccacagc tttggctctc    180
tccaagttct cacctgacct caggcttgtg attggaggtc gaaacaggga gaaggtgat    240 gctgtagtgt ctaaactagg agaaaactcc gagtttgttg aagtcaacgt tgacagtgtg    300
agatctttag aatctgctct cgaagatgtg gaccttgtag ttcatgcagc tggacctttt    360
caacaagcgg agaagtgcac tgttctagaa gctgcaatat ctaccaggac ggcctatgtg    420
gatgtatgtg ataatacaag ttattccatg caagcaaagt cttttcatga taaagcagtg    480
gctgccaacg ttcctgccat aacaactgct ggaattttcc ctggagtgag caatgtgata    540
gcagctgagc tagtgcgatc agcaagagat gaaaacactg aacctcaaag actaagattc    600 tcctattta ccgcgggttc tggtggtgct ggtccaacgt cgttagttac tagcttcttg     660
cttcttggtg aagaggttgt tgcttacagt gaaggcgaaa aagtcgaatt aaagccttat    720
acagggaagc ttaacattga cttcgggaag ggagttggga aagagacgt ttatttgtgg     780 aacttgccgg aagtaagaag tggtcatgag atcttaggag taccaactgt gagtgctcga    840
ttcggtactg cacctttctt ctggaattgg gcgatggtag ctatgacaac tctccttcct    900
cctggtattc tgagagacag aaataaaatc ggaatgttgg caaattttgt gtaccttct    960 gtacaaattt tgatgggat tgcaggagaa tgtcttgcaa tgcggttga tttagagtgc    1020 gcaaatgggc gcaatacttt tggtatactc agtcatgaac gtctctctgt attagtggga   1080
```

-continued

```
acttcaactg cggtgtttgc tatggcaatt cttgaaggaa gtacgcagcc tggagtttgg      1140
tttccagaag agcctggagg gattgcaata agtgacagag agttacttct acaacgagca      1200
tcacaaggag cgattaactt cattatgaag cagtagagta atagattgga ttattcatta      1260
tgtagcccag aatgacatta tttacatgta atgttgcttc tatgtatcaa taacataaat      1320
cacaagtcat tcgtatttat ataagtattc agtccatatc tgggagcaaa aaaaaaaaa      1380 aaaaaaa                                                                1387
```

<210> SEQ ID NO 6
<211> LENGTH: 407
<212> TYPE: PRT
<213> ORGANISM: Adonis aestivalis

<400> SEQUENCE: 6

```
Met Ala Pro Val Leu Leu Gly Leu Lys Pro Thr Leu Ser Thr Gly Ser
 1               5                  10                  15

Val Val Lys Glu Thr Asn Val Gly Ser Thr Leu Ala Ser Pro Leu Asn
            20                  25                  30

Lys Thr Gln Asn Ser Arg Val Leu Val Leu Gly Gly Thr Gly Lys Val
        35                  40                  45

Gly Gly Ser Thr Ala Leu Ala Leu Ser Lys Phe Ser Pro Asp Leu Arg
    50                  55                  60

Leu Val Ile Gly Gly Arg Asn Arg Glu Lys Gly Asp Ala Val Val Ser
65                  70                  75                  80

Lys Leu Gly Glu Asn Ser Glu Phe Val Glu Val Asn Val Asp Ser Val
                85                  90                  95

Arg Ser Leu Glu Ser Ala Leu Glu Asp Val Asp Leu Val Val His Ala
            100                 105                 110

Ala Gly Pro Phe Gln Gln Ala Glu Lys Cys Thr Val Leu Glu Ala Ala
        115                 120                 125

Ile Ser Thr Arg Thr Ala Tyr Val Asp Val Cys Asp Asn Thr Ser Tyr
    130                 135                 140

Ser Met Gln Ala Lys Ser Phe His Asp Lys Ala Val Ala Ala Asn Val
145                 150                 155                 160

Pro Ala Ile Thr Thr Ala Gly Ile Phe Pro Gly Val Ser Asn Val Ile
                165                 170                 175

Ala Ala Glu Leu Val Arg Ser Ala Arg Asp Glu Asn Thr Glu Pro Gln
            180                 185                 190

Arg Leu Arg Phe Ser Tyr Phe Thr Ala Gly Ser Gly Ala Gly Pro
        195                 200                 205

Thr Ser Leu Val Thr Ser Phe Leu Leu Leu Gly Glu Glu Val Val Ala
    210                 215                 220

Tyr Ser Glu Gly Glu Lys Val Glu Leu Lys Pro Tyr Thr Gly Lys Leu
225                 230                 235                 240

Asn Ile Asp Phe Gly Lys Gly Val Gly Lys Arg Asp Val Tyr Leu Trp
                245                 250                 255

Asn Leu Pro Glu Val Arg Ser Gly His Glu Ile Leu Gly Val Pro Thr
            260                 265                 270

Val Ser Ala Arg Phe Gly Thr Ala Pro Phe Phe Trp Asn Trp Ala Met
        275                 280                 285

Val Ala Met Thr Thr Leu Leu Pro Pro Gly Ile Leu Arg Asp Arg Asn
    290                 295                 300

Lys Ile Gly Met Leu Ala Asn Phe Val Tyr Pro Ser Val Gln Ile Phe
305                 310                 315                 320
```

```
Asp Gly Ile Ala Gly Glu Cys Leu Ala Met Arg Val Asp Leu Glu Cys
            325                 330                 335

Ala Asn Gly Arg Asn Thr Phe Gly Ile Leu Ser His Glu Arg Leu Ser
            340                 345                 350

Val Leu Val Gly Thr Ser Thr Ala Val Phe Ala Met Ala Ile Leu Glu
            355                 360                 365

Gly Ser Thr Gln Pro Gly Val Trp Phe Pro Glu Glu Pro Gly Gly Ile
        370                 375                 380

Ala Ile Ser Asp Arg Glu Leu Leu Gln Arg Ala Ser Gln Gly Ala
385                 390                 395                 400

Ile Asn Phe Ile Met Lys Gln
            405

<210> SEQ ID NO 7
<211> LENGTH: 428
<212> TYPE: PRT
<213> ORGANISM: Arabidopsis thaliana

<400> SEQUENCE: 7

Met Thr Arg Ala Leu Leu Leu Gln Pro Tyr Arg Ala Thr Val Arg Ala
1               5                   10                  15

Ala Ser Ser Arg Glu Thr Gln Tyr Asp Gly Val Pro Glu Val Lys Phe
            20                  25                  30

Ser Asp Pro Ser Arg Asn Tyr Arg Val Leu Val Leu Gly Gly Thr Gly
        35                  40                  45

Arg Val Gly Gly Ser Thr Ala Thr Ala Leu Ser Lys Leu Cys Pro Glu
    50                  55                  60

Leu Lys Ile Val Gly Gly Arg Asn Arg Glu Lys Gly Glu Ala Met
65                  70                  75                  80

Val Ala Lys Leu Gly Glu Asn Ser Glu Phe Ser Gln Val Asp Ile Asn
            85                  90                  95

Asp Ala Lys Met Leu Glu Thr Ser Leu Arg Asp Val Asp Leu Val Val
            100                 105                 110

His Ala Ala Gly Pro Phe Gln Gln Ala Pro Arg Cys Thr Val Leu Glu
            115                 120                 125

Ala Ala Ile Lys Thr Lys Thr Ala Tyr Leu Asp Val Cys Asp Asp Thr
        130                 135                 140

Ser Tyr Ala Phe Arg Ala Lys Ser Leu Glu Ala Glu Ala Ile Ala Ala
145                 150                 155                 160

Asn Ile Pro Ala Leu Thr Thr Ala Gly Ile Tyr Pro Gly Val Ser Asn
            165                 170                 175

Val Met Ala Ala Glu Met Val Ala Ala Arg Ser Glu Asp Lys Gly
            180                 185                 190

Lys Pro Glu Lys Leu Arg Phe Ser Tyr Tyr Thr Ala Gly Thr Gly Gly
        195                 200                 205

Ala Gly Pro Thr Ile Leu Ala Thr Ser Phe Leu Leu Leu Gly Glu Glu
    210                 215                 220

Val Thr Ala Tyr Lys Gln Gly Glu Lys Val Lys Leu Arg Pro Tyr Ser
225                 230                 235                 240

Gly Met Ile Thr Val Asp Phe Gly Lys Gly Ile Arg Lys Arg Asp Val
            245                 250                 255

Tyr Leu Leu Asn Leu Pro Glu Val Arg Ser Thr His Glu Val Leu Gly
            260                 265                 270

Val Pro Thr Val Val Ala Arg Phe Gly Thr Ala Pro Phe Phe Trp Asn
        275                 280                 285
```

-continued

```
Trp Gly Met Glu Ile Met Thr Lys Leu Leu Pro Ser Glu Val Leu Arg
        290                 295                 300

Asp Arg Thr Lys Val Gln Gln Met Val Glu Leu Phe Asp Pro Val Val
305                 310                 315                 320

Arg Ala Met Asp Gly Phe Ala Gly Glu Arg Val Ser Met Arg Val Asp
                325                 330                 335

Leu Glu Cys Ser Asp Gly Arg Thr Thr Val Gly Leu Phe Ser His Lys
            340                 345                 350

Lys Leu Ser Val Ser Val Gly Val Ser Thr Ala Ala Phe Val Ala Ala
        355                 360                 365

Met Leu Glu Gly Ser Thr Gln Pro Gly Val Trp Phe Pro Glu Glu Pro
    370                 375                 380

Gln Gly Ile Ala Val Glu Ala Arg Glu Val Leu Leu Lys Arg Ala Ser
385                 390                 395                 400

Gln Gly Thr Phe Asn Phe Ile Leu Asn Lys Pro Pro Trp Met Val Glu
                405                 410                 415

Thr Glu Pro Lys Glu Val Val Leu Gly Ile Tyr Val
            420                 425
```

<210> SEQ ID NO 8
<211> LENGTH: 45
<212> TYPE: PRT
<213> ORGANISM: Adonis aestivalis

<400> SEQUENCE: 8

```
Met Thr Met Ile Thr Pro Ser Ser Lys Leu Thr Leu Thr Lys Gly Asn
1               5                   10                  15

Lys Ser Trp Ser Ser Thr Ala Val Ala Ala Leu Glu Leu Val Asp
            20                  25                  30

Pro Pro Gly Cys Arg Asn Ser His Glu Glu Glu His Tyr
        35                  40                  45
```

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
cacaccatgg ctcctgttct ccttg     25

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
ctgggctaca taatgaataa tccaatc     27

<210> SEQ ID NO 11
<211> LENGTH: 1375
<212> TYPE: DNA
<213> ORGANISM: Adonis aestivalis

```
<400> SEQUENCE: 11
gaacattaca tggcgcgtgt cttccttgga ttgaaaccaa ctctctccac tggaagctcg      60
tcaaagagac tactgtagga aacacacttg ttagtcccct aacaaaacc cagaattcaa     120 gggttttggt tttgggcgga acagggaagg tcggtggttc cacagctttc gctctctcca    180
agttctcacc tgacctcagg cttgtgattg aggtcgaaa cagggagaaa ggtgatgctg      240
tagtgtctaa actaggagaa aactccgagt ttgttgaagt caacgttgac agcatgagat    300
ctttagaatc tgccttcaaa gatgtggatc ttgtagttca tgcagctgga ccttttcaac    360
aagcggagaa gtgcactgtt ctagaagctg caatatctac caggacggcc tatgtggatg    420
tatgtgataa tacaagttac tccatgcaag ctaagtcttt tcatgataaa gcagtggctg    480
ccaacgttcc tgccataaca actgctggaa ttttccctgg agtgagcaat gtgatagcag    540
ctgagctagt gcgatcagca agagatgaaa acactgaacc tcaaagacta agattctcct    600
attttaccgc gggttctggt ggtgctggtc caacctcgtt agttactagc tttttgcttc    660
ttggtgaaga ggttgttgct tacagtgaag gtgaaaaggt cgaattaaag ccttatacag    720
ggaagcttaa cattgacttc gggaagggag ttggaaaaag agacgtttat tgtggaact     780 tacccgaagt aagaagtggt catgagatct taggagtacc aactgtgagt gctcgattcg    840
gtactgcacc tttcttctgg aattgggcga tggtagctat gacaagtctc cttcctcctg    900
gtattctgag agacagaaat ataattgaaa agttggcaaa ttttgtctac ccttctgtac    960 aagttttttga tggtattgca ggagaatgtc tggctatgcg ggttgatttg gagtgcgcaa   1020
atgggcgcaa cacttctgct atactcagtc acgaacgtct ctctgaatta gtgggaactt    1080
caaccgcggt gtttgctttg caattcttg agggaagtac acaggctggt gtttggtttc    1140
cagaagagcc cgagggatt gcagtaggag acagagaatt acttctaaaa cgagcatcac     1200
aaggagctat taacttcatt atgaagcagt agagcaatag attggattat tcattatgta    1260
gccaagaata acattattta catgtaatgt tccttctatg tatcaataac atacatttta    1320
catgttatct ctaatggaaa ttttagatga actcaaaaaa aaaaaaaaaa aaaaa         1375

<210> SEQ ID NO 12
<211> LENGTH: 409
<212> TYPE: PRT
<213> ORGANISM: Adonis aestivalis

<400> SEQUENCE: 12

Thr Leu His Gly Ala Cys Leu Pro Trp Ile Glu Thr Asn Ser Leu His
 1               5                  10                  15

Trp Lys Leu Val Lys Glu Thr Thr Val Gly Asn Thr Leu Val Ser Pro
             20                  25                  30

Leu Asn Lys Thr Gln Asn Ser Arg Val Leu Val Leu Gly Gly Thr Gly
         35                  40                  45

Lys Val Gly Gly Ser Thr Ala Phe Ala Leu Ser Lys Phe Ser Pro Asp
     50                  55                  60

Leu Arg Leu Val Ile Gly Gly Arg Asn Arg Glu Lys Gly Asp Ala Val
 65                  70                  75                  80

Val Ser Lys Leu Gly Glu Asn Ser Glu Phe Val Glu Val Asn Val Asp
                 85                  90                  95

Ser Met Arg Ser Leu Glu Ser Ala Phe Lys Asp Val Asp Leu Val Val
            100                 105                 110

His Ala Ala Gly Pro Phe Gln Gln Ala Glu Lys Cys Thr Val Leu Glu
        115                 120                 125
```

-continued

| Ala | Ala | Ile | Ser | Thr | Arg | Thr | Ala | Tyr | Val | Asp | Val | Cys | Asp | Asn | Thr |
| | 130 | | | | | 135 | | | | | 140 | | | | |

| Ser | Tyr | Ser | Met | Gln | Ala | Lys | Ser | Phe | His | Asp | Lys | Ala | Val | Ala | Ala |
| 145 | | | | | 150 | | | | | 155 | | | | | 160 |

| Asn | Val | Pro | Ala | Ile | Thr | Thr | Ala | Gly | Ile | Phe | Pro | Gly | Val | Ser | Asn |
| | | | | 165 | | | | | 170 | | | | | 175 | |

| Val | Ile | Ala | Ala | Glu | Leu | Val | Arg | Ser | Ala | Arg | Asp | Glu | Asn | Thr | Glu |
| | | | 180 | | | | | 185 | | | | | 190 | | |

| Pro | Gln | Arg | Leu | Arg | Phe | Ser | Tyr | Phe | Thr | Ala | Gly | Ser | Gly | Gly | Ala |
| | | 195 | | | | | 200 | | | | | 205 | | | |

| Gly | Pro | Thr | Ser | Leu | Val | Thr | Ser | Phe | Leu | Leu | Leu | Gly | Glu | Glu | Val |
| | 210 | | | | | 215 | | | | | 220 | | | | |

| Val | Ala | Tyr | Ser | Glu | Gly | Glu | Lys | Val | Glu | Leu | Lys | Pro | Tyr | Thr | Gly |
| 225 | | | | | 230 | | | | | 235 | | | | | 240 |

| Lys | Leu | Asn | Ile | Asp | Phe | Gly | Lys | Gly | Val | Gly | Lys | Arg | Asp | Val | Tyr |
| | | | | 245 | | | | | 250 | | | | | 255 | |

| Leu | Trp | Asn | Leu | Pro | Glu | Val | Arg | Ser | Gly | His | Glu | Ile | Leu | Gly | Val |
| | | | 260 | | | | | 265 | | | | | 270 | | |

| Pro | Thr | Val | Ser | Ala | Arg | Phe | Gly | Thr | Ala | Pro | Phe | Phe | Trp | Asn | Trp |
| | | 275 | | | | | 280 | | | | | 285 | | | |

| Ala | Met | Val | Ala | Met | Thr | Ser | Leu | Leu | Pro | Pro | Gly | Ile | Leu | Arg | Asp |
| | 290 | | | | | 295 | | | | | 300 | | | | |

| Arg | Asn | Ile | Ile | Glu | Lys | Leu | Ala | Asn | Phe | Val | Tyr | Pro | Ser | Val | Gln |
| 305 | | | | | 310 | | | | | 315 | | | | | 320 |

| Val | Phe | Asp | Gly | Ile | Ala | Gly | Glu | Cys | Leu | Ala | Met | Arg | Val | Asp | Leu |
| | | | | 325 | | | | | 330 | | | | | 335 | |

| Glu | Cys | Ala | Asn | Gly | Arg | Asn | Thr | Ser | Ala | Ile | Leu | Ser | His | Glu | Arg |
| | | | 340 | | | | | 345 | | | | | 350 | | |

| Leu | Ser | Glu | Leu | Val | Gly | Thr | Ser | Thr | Ala | Val | Phe | Ala | Leu | Ala | Ile |
| | | 355 | | | | | 360 | | | | | 365 | | | |

| Leu | Glu | Gly | Ser | Thr | Gln | Ala | Gly | Val | Trp | Phe | Pro | Glu | Glu | Pro | Glu |
| | 370 | | | | | 375 | | | | | 380 | | | | |

| Gly | Ile | Ala | Val | Gly | Asp | Arg | Glu | Leu | Leu | Leu | Lys | Arg | Ala | Ser | Gln |
| 385 | | | | | 390 | | | | | 395 | | | | | 400 |

| Gly | Ala | Ile | Asn | Phe | Ile | Met | Lys | Gln |
| | | | | 405 | | | | |

<210> SEQ ID NO 13
<211> LENGTH: 1314
<212> TYPE: DNA
<213> ORGANISM: Adonis aestivalis

<400> SEQUENCE: 13

```
gaacattaca tggctcctgt tctccttgga ttgaaaccaa ctctctccac tggaagcgtc      60
gtcaaagaga ctaatgtagg aagcacactt gctagtcccc ttaacaaaac ccagaattca     120
agggttttgg ttttgggcgg aacagggaag gtcggtggtt ccacagcttt ggctctctcc     180
aagttctcac ctgacctcag gcttgtgatt ggaggtcgaa acaggagaa aggtgatgct      240
gtagtgtcta aactaggaga aaactccgag tttgttgaag tcaacgttga cagtgtgaga     300
tctttagaat ctgctctcga agatgtggac cttgtagttc atgcagctgg accttttcaa     360
caagcggaga agtgcactgt tctagaagct gcaatatcta ccaggacggc ctatgtggat     420
gtatgtgata atacaagtta ttccatgcaa gcaaagtctt tcatgataaa gcagtggct      480
gccaacgttc ctgccataac aactgctgga attttccctg gagtgagcaa tgtgatagca     540
```

```
gctgagctag tgcgatcagc aagagatgaa acactgaac  ctcaaagact aagattctcc    600
tattttaccg cgggttctgg tggtgctggt ccaacgtcgt tagttactag cttcttgctt    660
cttggtgaag aggttgttgc ttacagtgaa ggcgaaaaag tcgaattaaa gccttataca    720
gggaagctta acattgactt cgggaaggga gttgggaaaa gagacgttta tttgtggaac    780
ttgccggaag taagaagtgg tcatgagatc ttaggagtac aactgtgag  tgctcgattc    840 ggtactgcac ctttcttctg gaattgggcg atggtagcta tgacaactct ccttcctcct    900
ggtattctga gagacagaaa taaaatcgga atgttggcaa attttgtgta cccttctgta    960 caaattttg  atgggattgc aggagaatgt cttgcaatgc gggttgattt agagtgcgca   1020
aatgggcgca atacttttgg tatactcagt catgaacgtc tctctgtatt agtgggaact   1080
tcaactgcgg tgtttgctat ggcaattctt gaaggaagta cgcagcctgg agtttggttt   1140
ccagaagagc ctggagggat tgcaataagt gacagagagt tacttctaca acgagcatca   1200
caaggagcga ttaacttcat tatgaagcag tagagtaata gattggatta ttcattatgt   1260
agcccagaat gacattattt acatgtaatg ttgcttctat gtatcaataa cata          1314

<210> SEQ ID NO 14
<211> LENGTH: 1313
<212> TYPE: DNA
<213> ORGANISM: Adonis aestivalis

<400> SEQUENCE: 14
gaacattaca tggcgcgtgt cttccttgga ttgaaaccaa ctctctccac tggaagctcg     60
tcaaagagac tactgtagga acacacttg  ttagtcccct taacaaaacc cagaattcaa    120
gggttttggt tttgggcgga acagggaagg tcggtggttc cacagctttc gctctctcca    180
agttctcacc tgacctcagg cttgtgattg aggtcgaaa  cagggagaaa ggtgatgctg    240
tagtgtctaa actaggagaa aactccgagt ttgttgaagt caacgttgac agcatgagat    300
ctttagaatc tgccttcaaa gatgtggatc ttgtagttca tgcagctgga ccttttcaac    360
aagcggagaa gtgcactgtt ctagaagctg caatatctac caggacggcc tatgtggatg    420
tatgtgataa tacaagttac tccatgcaag ctaagtcttt tcatgataaa gcagtggctg    480
ccaacgttcc tgccataaca actgctggaa ttttccctgg agtgagcaat gtgatagcag    540
ctgagctagt gcgatcagca agagatgaaa acactgaacc tcaaagacta agattctcct    600
attttaccgc gggttctggt ggtgctggtc caacctcgtt agttactagc ttttttgcttc    660 ttggtgaaga ggttgttgct tacagtgaag gtgaaaaggt cgaattaaag ccttatacag    720
ggaagcttaa cattgacttc gggaaggag  ttggaaaaag agacgtttat ttgtggaact    780
tacccgaagt aagaagtggt catgagatct taggagtacc aactgtgagt gctcgattcg    840
gtactgcacc tttcttctgg aattgggcga tggtagctat gacaagtctc cttcctcctg    900
gtattctgag agacagaaat ataattgaaa agttggcaaa ttttgtctac ccttctgtac    960 aagttttga  tggtattgca ggagaatgtc tggctatgcg ggttgatttg gagtgcgcaa   1020
atgggcgcaa cacttctgct atactcagtc acgaacgtct ctctgaatta gtgggaactc   1080
caaccgcggt gtttgctttg gcaattcttg agggaagtac acaggctggt gtttggtttc   1140
cagaagagcc cgagggatt  gcagtaggag acagagaatt acttctaaaa cgagcatcac   1200
aaggagctat taacttcatt atgaagcagt agagcaatag attggattat tcattatgta   1260
gccaagaata acattattta catgtaatgt tccttctatg tatcaataac ata           1313
```

-continued

```
<210> SEQ ID NO 15
<211> LENGTH: 390
<212> TYPE: PRT
<213> ORGANISM: Adonis aestivalis

<400> SEQUENCE: 15
```

| | | | | | | | | | | | | | | |
|---|---|---|---|---|---|---|---|---|---|---|---|---|---|---|
| Val | Lys | Glu | Thr | Asn | Val | Gly | Ser | Thr | Leu | Ala | Ser | Pro | Leu | Asn | Lys |
| 1 | | | | 5 | | | | | 10 | | | | | 15 | |

| Thr | Gln | Asn | Ser | Arg | Val | Leu | Val | Leu | Gly | Gly | Thr | Gly | Lys | Val | Gly |
|---|---|---|---|---|---|---|---|---|---|---|---|---|---|---|---|
| | | | 20 | | | | | 25 | | | | | 30 | | |

| Gly | Ser | Thr | Ala | Leu | Ala | Leu | Ser | Lys | Phe | Ser | Pro | Asp | Leu | Arg | Leu |
|---|---|---|---|---|---|---|---|---|---|---|---|---|---|---|---|
| | | 35 | | | | | 40 | | | | | 45 | | | |

| Val | Ile | Gly | Gly | Arg | Asn | Arg | Glu | Lys | Gly | Asp | Ala | Val | Val | Ser | Lys |
|---|---|---|---|---|---|---|---|---|---|---|---|---|---|---|---|
| | 50 | | | | | 55 | | | | | 60 | | | | |

| Leu | Gly | Glu | Asn | Ser | Glu | Phe | Val | Glu | Val | Asn | Val | Asp | Ser | Val | Arg |
|---|---|---|---|---|---|---|---|---|---|---|---|---|---|---|---|
| 65 | | | | | 70 | | | | | 75 | | | | | 80 |

| Ser | Leu | Glu | Ser | Ala | Leu | Glu | Asp | Val | Asp | Leu | Val | Val | His | Ala | Ala |
|---|---|---|---|---|---|---|---|---|---|---|---|---|---|---|---|
| | | | | 85 | | | | | 90 | | | | | 95 | |

| Gly | Pro | Phe | Gln | Gln | Ala | Glu | Lys | Cys | Thr | Val | Leu | Glu | Ala | Ala | Ile |
|---|---|---|---|---|---|---|---|---|---|---|---|---|---|---|---|
| | | | 100 | | | | | 105 | | | | | 110 | | |

| Ser | Thr | Arg | Thr | Ala | Tyr | Val | Asp | Val | Cys | Asp | Asn | Thr | Ser | Tyr | Ser |
|---|---|---|---|---|---|---|---|---|---|---|---|---|---|---|---|
| | | 115 | | | | | 120 | | | | | 125 | | | |

| Met | Gln | Ala | Lys | Ser | Phe | His | Asp | Lys | Ala | Val | Ala | Ala | Asn | Val | Pro |
|---|---|---|---|---|---|---|---|---|---|---|---|---|---|---|---|
| | 130 | | | | | 135 | | | | | 140 | | | | |

| Ala | Ile | Thr | Thr | Ala | Gly | Ile | Phe | Pro | Gly | Val | Ser | Asn | Val | Ile | Ala |
|---|---|---|---|---|---|---|---|---|---|---|---|---|---|---|---|
| 145 | | | | | 150 | | | | | 155 | | | | | 160 |

| Ala | Glu | Leu | Val | Arg | Ser | Ala | Arg | Asp | Glu | Asn | Thr | Glu | Pro | Gln | Arg |
|---|---|---|---|---|---|---|---|---|---|---|---|---|---|---|---|
| | | | | 165 | | | | | 170 | | | | | 175 | |

| Leu | Arg | Phe | Ser | Tyr | Phe | Thr | Ala | Gly | Ser | Gly | Ala | Gly | Pro | Thr |
|---|---|---|---|---|---|---|---|---|---|---|---|---|---|---|
| | | | 180 | | | | | 185 | | | | | 190 | |

| Ser | Leu | Val | Thr | Ser | Phe | Leu | Leu | Gly | Glu | Glu | Val | Val | Ala | Tyr |
|---|---|---|---|---|---|---|---|---|---|---|---|---|---|---|
| | | 195 | | | | | 200 | | | | | 205 | | |

| Ser | Glu | Gly | Glu | Lys | Val | Glu | Leu | Lys | Pro | Tyr | Thr | Gly | Lys | Leu | Asn |
|---|---|---|---|---|---|---|---|---|---|---|---|---|---|---|---|
| | 210 | | | | | 215 | | | | | 220 | | | | |

| Ile | Asp | Phe | Gly | Lys | Gly | Val | Gly | Lys | Arg | Asp | Val | Tyr | Leu | Trp | Asn |
|---|---|---|---|---|---|---|---|---|---|---|---|---|---|---|---|
| 225 | | | | | 230 | | | | | 235 | | | | | 240 |

| Leu | Pro | Glu | Val | Arg | Ser | Gly | His | Glu | Ile | Leu | Gly | Val | Pro | Thr | Val |
|---|---|---|---|---|---|---|---|---|---|---|---|---|---|---|---|
| | | | | 245 | | | | | 250 | | | | | 255 | |

| Ser | Ala | Arg | Phe | Gly | Thr | Ala | Pro | Phe | Phe | Trp | Asn | Trp | Ala | Met | Val |
|---|---|---|---|---|---|---|---|---|---|---|---|---|---|---|---|
| | | | 260 | | | | | 265 | | | | | 270 | | |

| Ala | Met | Thr | Thr | Leu | Leu | Pro | Pro | Gly | Ile | Leu | Arg | Asp | Arg | Asn | Lys |
|---|---|---|---|---|---|---|---|---|---|---|---|---|---|---|---|
| | | 275 | | | | | 280 | | | | | 285 | | | |

| Ile | Gly | Met | Leu | Ala | Asn | Phe | Val | Tyr | Pro | Ser | Val | Gln | Ile | Phe | Asp |
|---|---|---|---|---|---|---|---|---|---|---|---|---|---|---|---|
| | 290 | | | | | 295 | | | | | 300 | | | | |

| Gly | Ile | Ala | Gly | Glu | Cys | Leu | Ala | Met | Arg | Val | Asp | Leu | Glu | Cys | Ala |
|---|---|---|---|---|---|---|---|---|---|---|---|---|---|---|---|
| 305 | | | | | 310 | | | | | 315 | | | | | 320 |

| Asn | Gly | Arg | Asn | Thr | Phe | Gly | Ile | Leu | Ser | His | Glu | Arg | Leu | Ser | Val |
|---|---|---|---|---|---|---|---|---|---|---|---|---|---|---|---|
| | | | | 325 | | | | | 330 | | | | | 335 | |

| Leu | Val | Gly | Thr | Ser | Thr | Ala | Val | Phe | Ala | Met | Ala | Ile | Leu | Glu | Gly |
|---|---|---|---|---|---|---|---|---|---|---|---|---|---|---|---|
| | | | 340 | | | | | 345 | | | | | 350 | | |

| Ser | Thr | Gln | Pro | Gly | Val | Trp | Phe | Pro | Glu | Glu | Pro | Gly | Ile | Ala |
|---|---|---|---|---|---|---|---|---|---|---|---|---|---|---|
| | | 355 | | | | | 360 | | | | | 365 | | |

```
Ile Ser Asp Arg Glu Leu Leu Leu Gln Arg Ala Ser Gln Gly Ala Ile
    370                 375                 380

Asn Phe Ile Met Lys Gln
385                 390

<210> SEQ ID NO 16
<211> LENGTH: 390
<212> TYPE: PRT
<213> ORGANISM: Adonis aestivalis

<400> SEQUENCE: 16

Val Lys Glu Thr Thr Val Gly Asn Thr Leu Val Ser Pro Leu Asn Lys
  1               5                  10                  15

Thr Gln Asn Ser Arg Val Leu Val Leu Gly Gly Thr Gly Lys Val Gly
                 20                  25                  30

Gly Ser Thr Ala Phe Ala Leu Ser Lys Phe Ser Pro Asp Leu Arg Leu
             35                  40                  45

Val Ile Gly Gly Arg Asn Arg Glu Lys Gly Asp Ala Val Val Ser Lys
         50                  55                  60

Leu Gly Glu Asn Ser Glu Phe Val Glu Val Asn Val Asp Ser Met Arg
 65                  70                  75                  80

Ser Leu Glu Ser Ala Phe Lys Asp Val Asp Leu Val Val His Ala Ala
                 85                  90                  95

Gly Pro Phe Gln Gln Ala Glu Lys Cys Thr Val Leu Glu Ala Ala Ile
            100                 105                 110

Ser Thr Arg Thr Ala Tyr Val Asp Val Cys Asp Asn Thr Ser Tyr Ser
        115                 120                 125

Met Gln Ala Lys Ser Phe His Asp Lys Ala Val Ala Ala Asn Val Pro
130                 135                 140

Ala Ile Thr Thr Ala Gly Ile Phe Pro Gly Val Ser Asn Val Ile Ala
145                 150                 155                 160

Ala Glu Leu Val Arg Ser Ala Arg Asp Glu Asn Thr Glu Pro Gln Arg
                165                 170                 175

Leu Arg Phe Ser Tyr Phe Thr Ala Gly Ser Gly Gly Ala Gly Pro Thr
            180                 185                 190

Ser Leu Val Thr Ser Phe Leu Leu Leu Gly Glu Glu Val Val Ala Tyr
        195                 200                 205

Ser Glu Gly Glu Lys Val Glu Leu Lys Pro Tyr Thr Gly Lys Leu Asn
    210                 215                 220

Ile Asp Phe Gly Lys Gly Val Gly Lys Arg Asp Val Tyr Leu Trp Asn
225                 230                 235                 240

Leu Pro Glu Val Arg Ser Gly His Glu Ile Leu Gly Val Pro Thr Val
                245                 250                 255

Ser Ala Arg Phe Gly Thr Ala Pro Phe Phe Trp Asn Trp Ala Met Val
            260                 265                 270

Ala Met Thr Ser Leu Leu Pro Pro Gly Ile Leu Arg Asp Arg Asn Ile
        275                 280                 285

Ile Glu Lys Leu Ala Asn Phe Val Tyr Pro Ser Val Gln Val Phe Asp
    290                 295                 300

Gly Ile Ala Gly Glu Cys Leu Ala Met Arg Val Asp Leu Glu Cys Ala
305                 310                 315                 320

Asn Gly Arg Asn Thr Ser Ala Ile Leu Ser His Glu Arg Leu Ser Glu
                325                 330                 335

Leu Val Gly Thr Ser Thr Ala Val Phe Ala Leu Ala Ile Leu Glu Gly
            340                 345                 350
```

-continued

```
Ser Thr Gln Ala Gly Val Trp Phe Pro Glu Glu Pro Glu Gly Ile Ala
        355                 360                 365

Val Gly Asp Arg Glu Leu Leu Leu Lys Arg Ala Ser Gln Gly Ala Ile
    370                 375                 380

Asn Phe Ile Met Lys Gln
385                 390
```